(12) United States Patent
Randall et al.

(10) Patent No.: US 7,077,996 B2
(45) Date of Patent: Jul. 18, 2006

(54) METHODS AND APPARATUS FOR BLOOD SEPARATION AND ANALYSIS USING MEMBRANES ON AN OPTICAL BIO-DISC

(76) Inventors: Brandon L. Randall, 1804 Skiles Blvd., West Chester, PA (US) 19382; Raveendra Pottathil, 8806 Cliffridge Ave., La Jolla, CA (US) 92037; Shuguang Li, 39 San Patrico, Rancho Santa Margarita, CA (US) 92688

( * ) Notice: Subject to any disclaimer, the term of this patent is extended or adjusted under 35 U.S.C. 154(b) by 0 days.

(21) Appl. No.: 10/891,442

(22) Filed: Jul. 13, 2004

(65) Prior Publication Data
US 2005/0130294 A1 Jun. 16, 2005

Related U.S. Application Data

(60) Provisional application No. 60/487,339, filed on Jul. 15, 2003.

(51) Int. Cl.
*G01N 15/06* (2006.01)
*G01N 33/00* (2006.01)
*G01N 33/48* (2006.01)

(52) U.S. Cl. .................. 422/68.1; 422/50; 422/56; 422/57; 422/58; 422/64; 422/72; 435/287.7; 435/287.9; 435/288.2; 435/288.5; 435/960; 435/970

(58) Field of Classification Search .................. 422/50, 422/56–58, 64, 68.1, 72, 258; 435/287.7, 435/287.9, 288.2, 288.5, 960, 970; 436/43, 436/45

See application file for complete search history.

(56) References Cited

U.S. PATENT DOCUMENTS

| 4,515,889 | A | * | 5/1985 | Klose et al. .................. 435/4 |
| 5,061,381 | A | | 10/1991 | Burd |
| 5,141,850 | A | * | 8/1992 | Cole et al. .................. 436/525 |
| 5,415,994 | A | * | 5/1995 | Imrich et al. .................. 435/5 |
| 5,417,650 | A | | 5/1995 | Gordon |
| 5,591,643 | A | | 1/1997 | Schembri |

(Continued)

Primary Examiner—Long V. Le
Assistant Examiner—Leon Y. Lum
(74) Attorney, Agent, or Firm—Knobbe, Martens, Olson & Bear, LLP

(57) ABSTRACT

Optical bio-discs for biochemical analysis, bio-disc analysis systems and biochemical analysis methods are described herein. In one embodiment, the bio-disc includes a sample analysis circuit that includes a separation membrane for separating an investigational feature of a sample. The bio-disc also includes a conjugate release pad, and an analysis membrane containing analysis zones that may be analyzed for the presence of analytes. An analysis method includes providing a sample to a separation membrane in a bio-disc, separating an investigational feature from the sample using a separation membrane, mixing reagents that include signal elements for detecting an analyte with the investigational feature so as to form a reagent-investigational feature mixture and capturing an analyte with a signal element bound thereto in an analysis zone on an analysis membrane. The method further includes determining the presence of an analyte by analyzing the signal elements present in the capture zone of the analysis membrane.

15 Claims, 18 Drawing Sheets

U.S. PATENT DOCUMENTS

| | | | |
|---|---|---|---|
| 5,824,216 A | * | 10/1998 | Joie et al. ............... 210/257.1 |
| 5,892,577 A | | 4/1999 | Gordon |
| 5,939,331 A | * | 8/1999 | Burd et al. ................ 436/518 |
| 6,030,581 A | | 2/2000 | Virtanen |
| 6,063,589 A | | 5/2000 | Kellogg et al. |
| 6,143,247 A | | 11/2000 | Sheppard, Jr. et al. |
| 6,143,248 A | * | 11/2000 | Kellogg et al. ............... 422/72 |
| 6,180,417 B1 | * | 1/2001 | Hajizadeh et al. .......... 436/518 |
| 6,319,469 B1 | * | 11/2001 | Mian et al. .................... 422/64 |
| 6,632,399 B1 | * | 10/2003 | Kellogg et al. ............... 422/72 |
| 2002/0076354 A1 | | 6/2002 | Cohen |

\* cited by examiner

Side View-Left

Side View-Right

METHODS AND APPARATUS FOR BLOOD SEPARATION AND ANALYSIS USING MEMBRANES ON AN OPTICAL BIO-DISC

RELATED APPLICATIONS

This application claims the benefit of U.S. Provisional Application No. 60/487,339 filed Jul. 15, 2003, the entirety of which is incorporated herein by reference in its entirety.

BACKGROUND

1. Field of the Invention

This invention relates in general to optical discs, optical disc drives and optical disc interrogation methods and, in particular, to methods and apparatus for blood separation. More specifically, but without restriction to the particular embodiments hereinafter described in accordance with the best mode of practice, this invention relates to optical discs including a lateral flow circuit having a blood separation membrane for immunohematologic analysis.

2. Description of the Related Technology

The Optical Bio-Disc, also referred to as Bio-Compact Disc (BCD), bio-optical disc, optical analysis disc or compact bio-disc, is known in the art for performing various types of bio-chemical analyses. In particular, this optical disc utilizes the laser source of an optical storage device to detect biochemical reactions on or near the operating surface of the disc itself. These reactions may be occurring in membranes on the disc, small channels inside the disc (frequently with one or more dimensions of less than 300 microns), or the reactions may be occurring on the open surface of the disc. Whatever the system, multiple reaction sites are usually needed either to simultaneously detect different reactions, or to repeat the same reaction for error detection purposes.

SUMMARY OF CERTAIN INVENTIVE ASPECTS

It is an object of the invention to overcome limitations in the known art.

Accordingly, the an embodiment is directed to blood separation and immunohematological analysis using an optical bio-disc, and to related disc drive systems and methods.

More specifically, the an embodiment is directed to an optical analysis bio-disc. The disc may advantageously include a substrate having an inner perimeter and an outer perimeter; an operational layer associated with the substrate and including encoded information located along information tracks; and an analysis area including investigational features, e.g., biological material. The analysis area is positioned between the inner perimeter and the outer perimeter and is directed along the information tracks so that when an incident beam of electromagnetic energy travels along them, the investigational features within the analysis area are thereby interrogated circumferentially. The analysis area may include reaction zones or target zones on a membrane.

An embodiment is also directed to an optical analysis disc as defined above, wherein when an incident beam of electromagnetic energy travels along the information tracks, the investigational features within the analysis area are interrogated according to a spiral path or, in general, according to a path of varying angular coordinate.

Preferably, the substrate includes a series of substantially circular information tracks that increase in circumference as a function of radius extending from the inner perimeter to the outer perimeter of the substrate. The analysis area is circumferentially elongated between a pre-selected number of circular information tracks and the investigational features are interrogated substantially along the circular information tracks between a pre-selected inner and outer circumference.

According to a preferred embodiment, the analysis area includes a membrane. Preferably, rotation of the bio-disc distributes investigational features in a substantially consistent distribution along the analysis area and/or in a substantially even distribution along the analysis area.

An embodiment is further directed to an optical analysis bio-disc. In this embodiment, the bio-disc includes a substrate having an inner perimeter and an outer perimeter; and an analysis zone including investigational features, the analysis zone being positioned between the inner perimeter and the outer perimeter of the substrate and extending according to a varying angular coordinate, and preferably according to a substantially circumferential or spiral path.

Preferably, the analysis zone extends according to a varying angular and radial coordinate. In an alternative embodiment, the analysis zone extends according to a varying angular coordinate and at a substantially fixed radial coordinate.

Preferably, the disc comprises an operational layer associated with the substrate and including encoded information located substantially along information tracks.

According to another preferred embodiment, the substrate includes a series of information tracks, preferably of a substantially circular profile and increasing in circumference as a function of radius extending from the inner perimeter to the outer perimeter, and the analysis zone is directed substantially along the information tracks, so that when an incident beam of electromagnetic energy tracks along the information tracks, the investigational features within the analysis zone are thereby interrogated circumferentially. More preferably, the analysis zone is circumferentially elongated between a pre-selected number of circular information tracks, and the investigational features are interrogated substantially along the circular information tracks between a pre-selected inner and outer circumference.

In another preferred embodiment, the analysis zone includes a plurality of reaction sites and/or a plurality of capture zones or target zones arranged according to a varying angular coordinate.

The optical analysis bio-disc may also include a plurality of analysis zones positioned between the inner perimeter and the outer perimeter of the substrate, at least one of which extends according to a varying angular coordinate.

Preferably, the analysis zones extend according to a substantially circumferential path and are concentrically arranged around the bio-disc inner perimeter.

In a variant embodiment, the disc includes multiple tiers of analysis zones, wherein each analysis zone extends according to a substantially circumferential path and each tier is arranged onto the bio-disc at a respective radial coordinate.

The disc may be either a reflective-type or transmissive-type optical bio-disc. As in previous embodiments, preferably rotation of the bio-disc distributes investigational features in a substantially consistent and/or even distribution along the analysis zone.

According to another preferred embodiment, the optical analysis bio-disc may include a substrate having an inner perimeter and an outer perimeter; and an analysis zone including investigational features and positioned between the inner perimeter and the outer perimeter of the substrate. The analysis zone includes at least a membrane or biomembrane The invention is also directed to an optical analysis bio-disc system for use with an optical analysis bio-disc as defined so far, which system includes interrogation devices of the investigational features adapted to interrogate the latter according to a varying angular coordinate.

Such interrogation devices may be configured so that when an incident beam of electromagnetic energy tracks along disc information tracks, any investigational features within the analysis zone are thereby interrogated circumferentially.

Preferably, the interrogation devices are adapted to interrogate the investigational features according to a varying angular coordinate at a substantially fixed radial coordinate or, alternatively, according to a varying angular and radial coordinate.

More preferably, the interrogation devices are employed to interrogate the investigational features according to a spiral or a substantially circumferential path.

According to a further preferred embodiment, the interrogation devices are utilized to interrogate investigational features at a plurality of reaction sites or capture or target zones arranged according to a varying angular coordinate.

The invention is also directed to a method for the interrogation of investigational features within an optical analysis bio-disc as defined so far. This method provides interrogation of the investigational features according to a varying angular coordinate, and preferably according to a spiral or a substantially circumferential path.

The interrogation step may also be performed such that when an incident beam of electromagnetic energy travels along disc information tracks, any investigational features within the analysis zone are thereby interrogated circumferentially.

Preferably, the interrogation step accomplishes interrogation of the investigational features according to a varying angular coordinate at a substantially fixed radial coordinate or, alternatively, according to a varying angular and radial coordinate.

According to a further preferred embodiment, the interrogation step provides interrogation of investigational features at a plurality of similar or different, reaction sites, capture zones, or target zones arranged according to a varying angular coordinate.

The embodiments and/or different aspects thereof may be readily implemented in or adapted to many of the discs, assays, and systems disclosed in the following commonly assigned and co-pending patent applications: U.S. patent application Ser. No. 09/378,878 entitled "Methods and Apparatus for Analyzing Operational and Non-operational Data Acquired from Optical Discs" filed Aug. 23, 1999; U.S. Provisional Application No. 60/291,233 entitled "Variable Sampling Control For Rendering Pixelation of Analysis Results In Optical Bio-Disc Assembly And Apparatus Relating Thereto" filed May 16, 2001; U.S. patent application Ser. No. 10/008,156 entitled "Disc Drive System and Methods for Use with Bio-discs" filed Nov. 9, 2001; U.S. patent application Ser. No. 10/043,688 entitled "Optical Disc Analysis System Including Related Methods for Biological and Medical Imaging" filed Jan. 10, 2002; U.S. patent application Ser. No. 10/348,196 entitled "Processes for Manufacturing Optical Analysis Discs with Molded Microfluidic Structures and Discs Made According Thereto" filed on Jan. 21, 2003; and U.S. Provisional Application No. 60/404,921 entitled "Methods For Differential Cell Counts Including Related Apparatus And Software For Performing Same" filed on Aug. 21, 2002, all which are herein incorporated by reference in their entireties. The above-referenced applications provide background and related disclosure as support hereof as if fully repeated herein.

BRIEF DESCRIPTION OF THE DRAWINGS

Further objects of the invention together with additional features contributing thereto and advantages accruing therefrom will be apparent from the following description of the preferred embodiments of the invention which are shown in the accompanying drawing figures with like reference numerals indicating like components throughout, wherein.

DETAILED DESCRIPTION OF CERTAIN INVENTIVE EMBODIMENTS

The invention is directed to disc drive systems, optical bio-discs, image processing techniques, analysis methods, and related software. Each of these aspects of the invention is discussed below in further detail.

Figure 1:
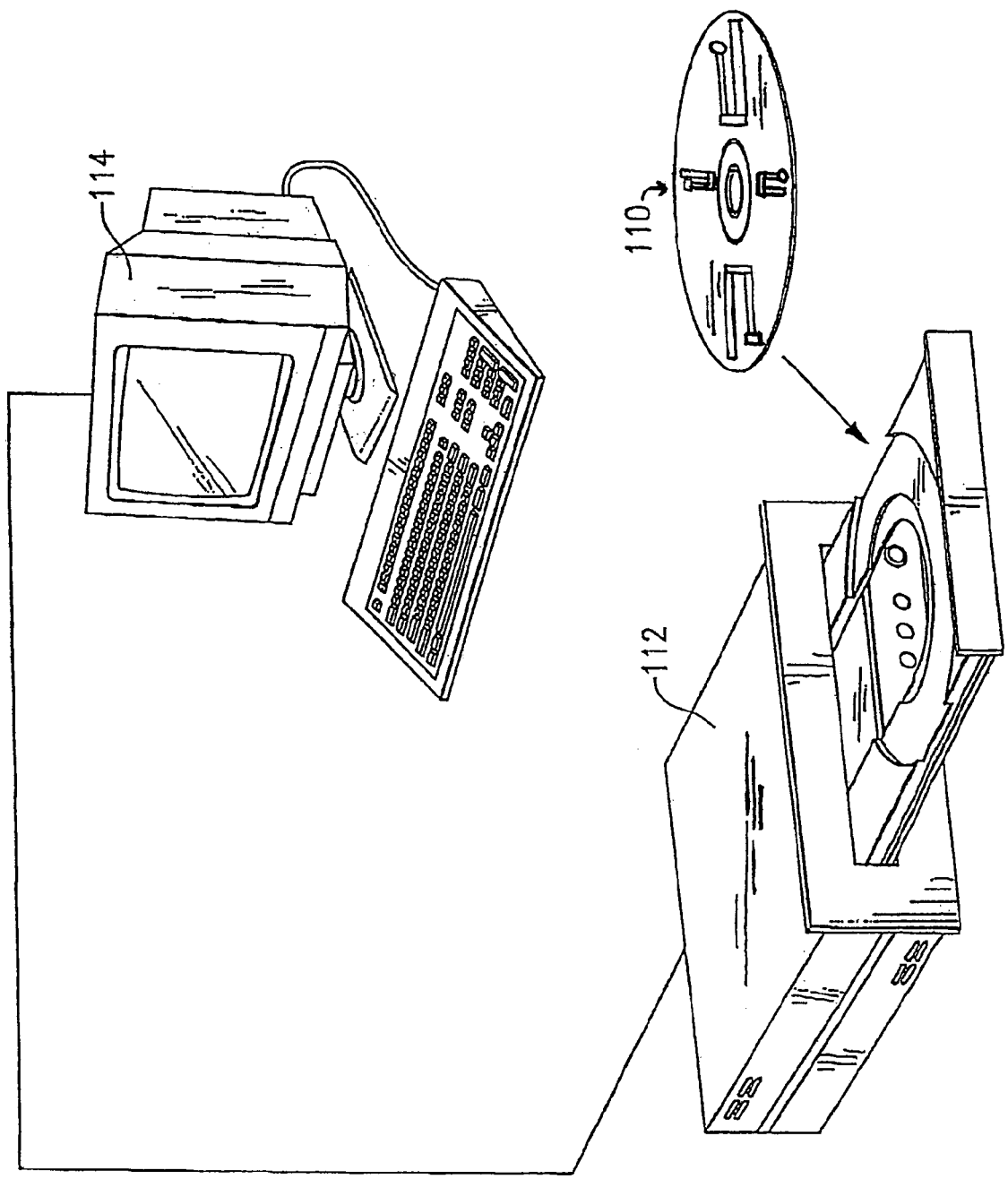
FIG. 1 is a pictorial representation of a bio-disc system.

FIG. 1 is a perspective view of an optical bio-disc 110 for conducting biochemical analyses, and in particular cell counts and differential cell counts. The optical bio-disc 110 is shown in conjunction with an optical disc drive 112 and a display monitor 114. Further details relating to this type of disc drive and disc analysis system are disclosed in commonly assigned and co-pending U.S. patent application Ser. No. 10/008,156 entitled "Disc Drive System and Methods for Use with Bio-discs" filed Nov. 9, 2001 and U.S. patent application Ser. No. 10/043,688 entitled "Optical Disc Analysis System Including Related Methods For Biological and Medical Imaging" filed Jan. 10, 2002, both of which are herein incorporated by reference.

Figure 2:
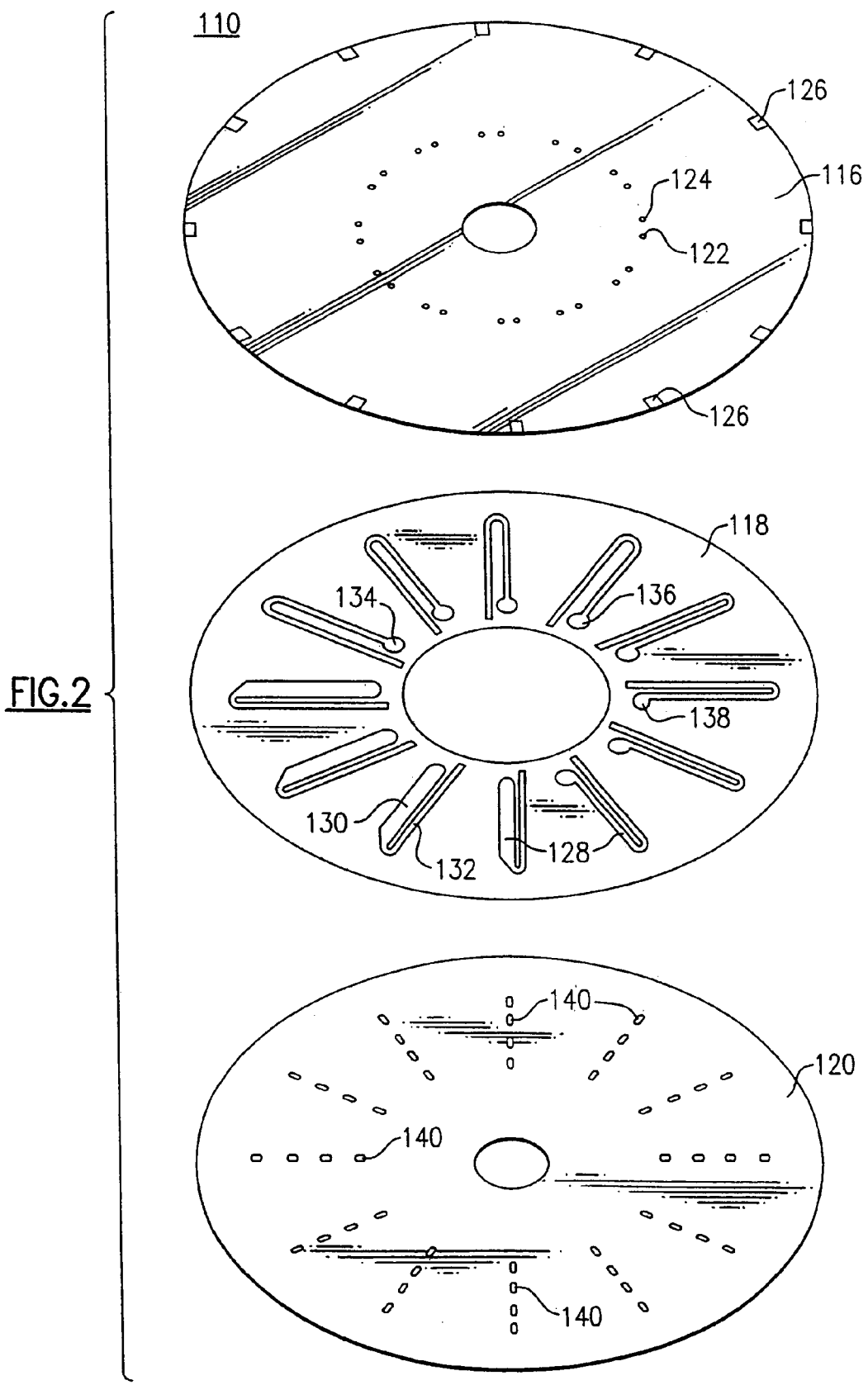
FIG. 2 is an exploded perspective view of a reflective bio-disc.
Figure 6:
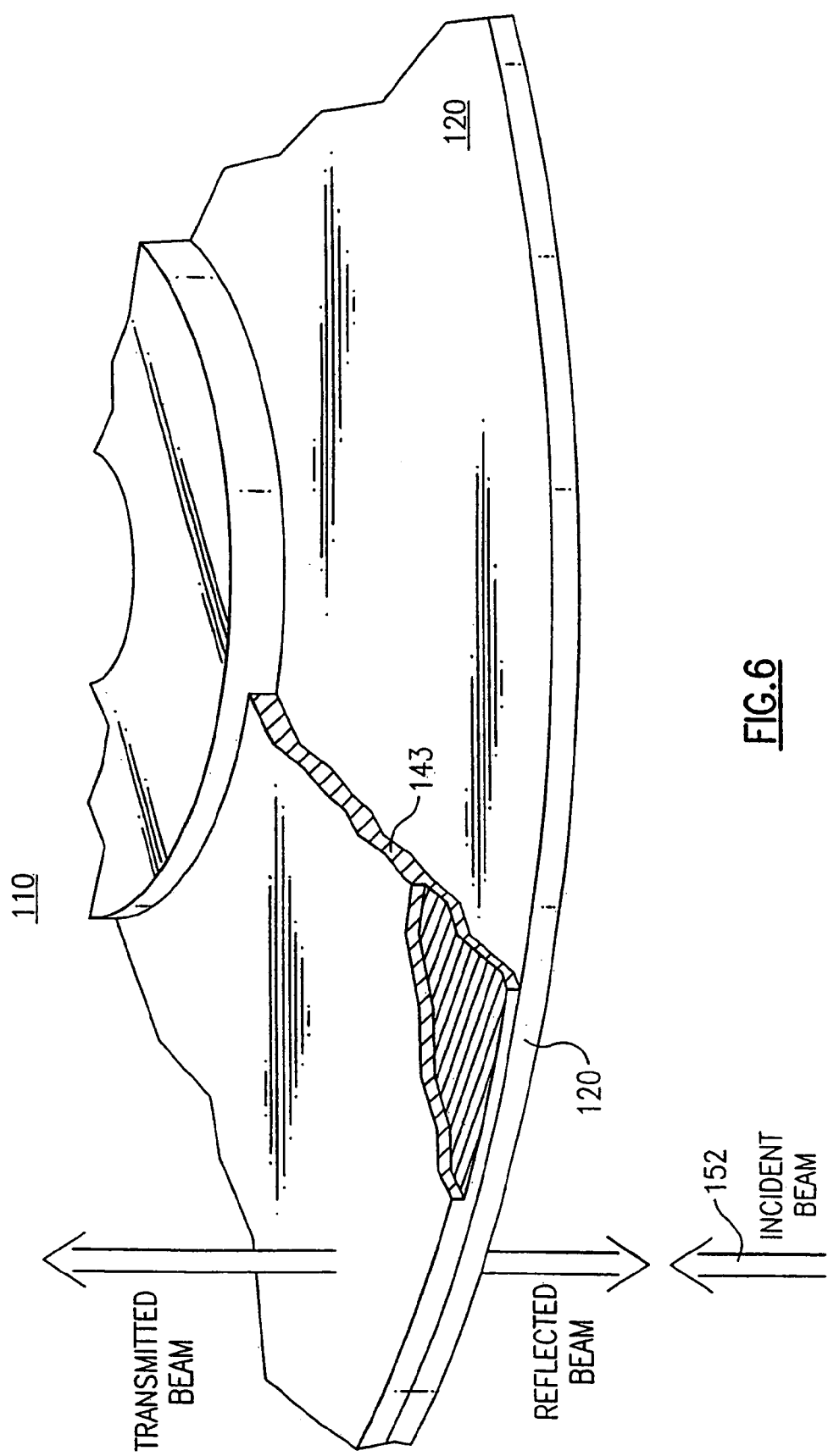
FIG. 6 is a perspective view representing the disc shown in FIG. 5 with a cut-away section illustrating the functional aspects of a semi-reflective layer of the disc.
Figure 10:
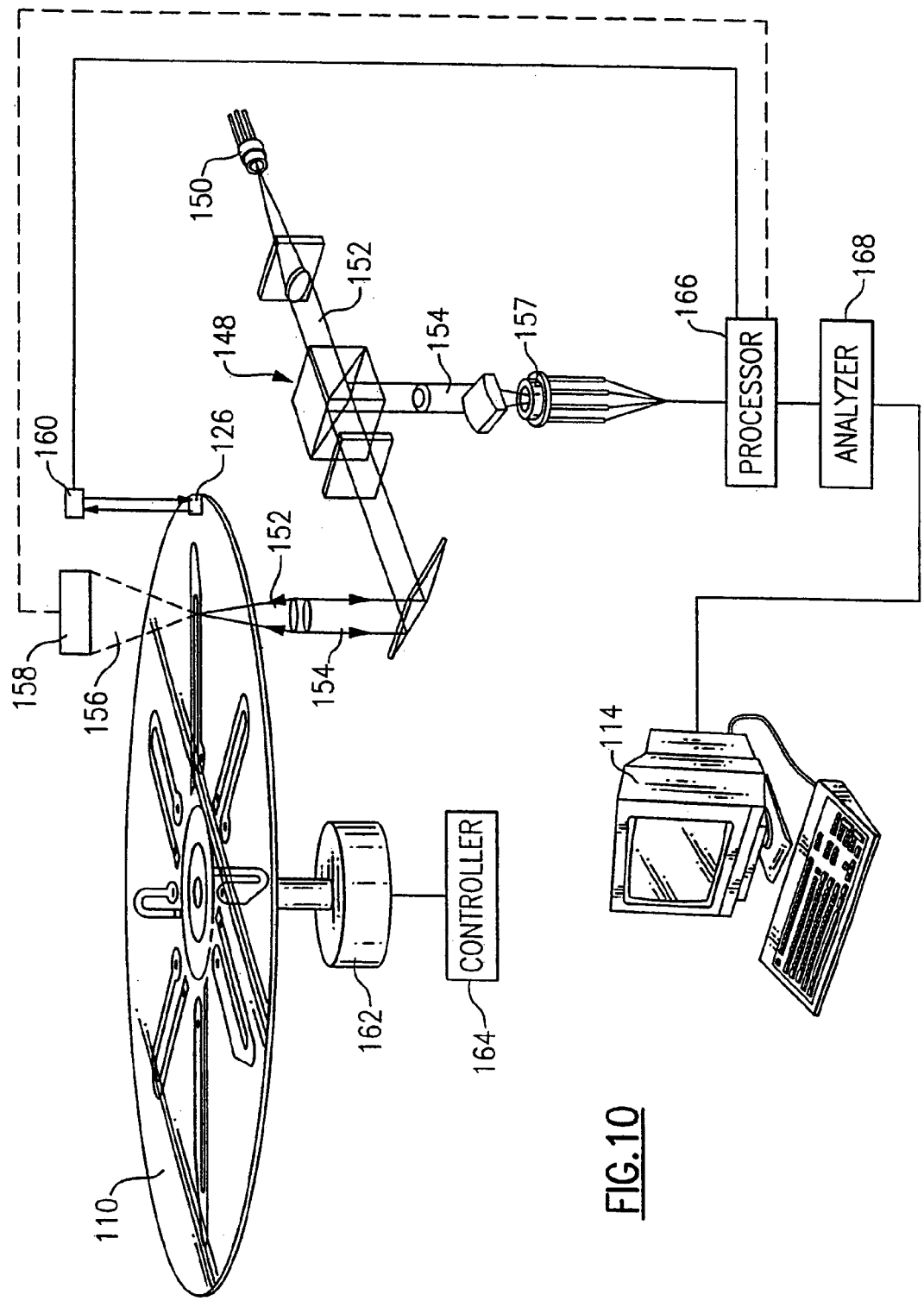
FIG. 10 is a perspective and block diagram representation illustrating the system of FIG. 1 in more detail.

FIG. 2 is an exploded perspective view of the principal structural elements of one embodiment of the optical bio-disc 110. FIG. 2 is an example of a reflective zone optical bio-disc 110 (hereinafter "reflective disc") that may be used in the invention. The principal structural elements include a cap portion 116, an adhesive member or channel layer 118, and a substrate 120. The cap portion 116 includes one or more inlet ports 122 and one or more vent ports 124. The cap portion 116 may be formed from polycarbonate and is preferably coated with a reflective surface 146 (shown in FIG. 4) on the bottom thereof as viewed from the perspective of FIG. 2. In the preferred embodiment, trigger marks or markings 126 are included on the surface of a reflective layer 142 (shown FIG. 4). Trigger markings 126 may include a clear window in all three layers of the bio-disc, an opaque area, or a reflective or semi-reflective area encoded with information that sends data to a processor 166, as shown FIG. 10, that in turn interacts with the operative functions of an interrogation or incident beam 152, as shown in FIGS. 6 and 10.

The second element shown in FIG. 2 is an adhesive member or channel layer 118 having fluidic circuits 128 or U-channels formed therein. The fluidic circuits 128 are formed by stamping or cutting the membrane to remove plastic film and form the shapes as indicated. Each of the fluidic circuits 128 includes a flow channel or analysis zone 130 and a return channel 132. Some of the fluidic circuits 128 illustrated in FIG. 2 include a mixing chamber 134. Two different types of mixing chambers 134 are illustrated. The first is a symmetric mixing chamber 136 that is symmetrically formed relative to the flow channel 130. The second is an off-set mixing chamber 138. The off-set mixing chamber 138 is formed to one side of the flow channel 130 as indicated.

The third element illustrated in FIG. 2 is a substrate 120 including target or capture zones 140. The substrate 120 is preferably made of polycarbonate and has the aforementioned reflective layer 142 deposited on the top thereof (shown in FIG. 4). The target zones 140 are formed by removing the reflective layer 142 in the indicated shape or alternatively in any desired shape. Alternatively, the target zone 140 may be formed by a masking technique that includes masking the target zone 140 area before applying the reflective layer 142. The reflective layer 142 may be formed from a metal such as aluminum or gold.

Figure 3:
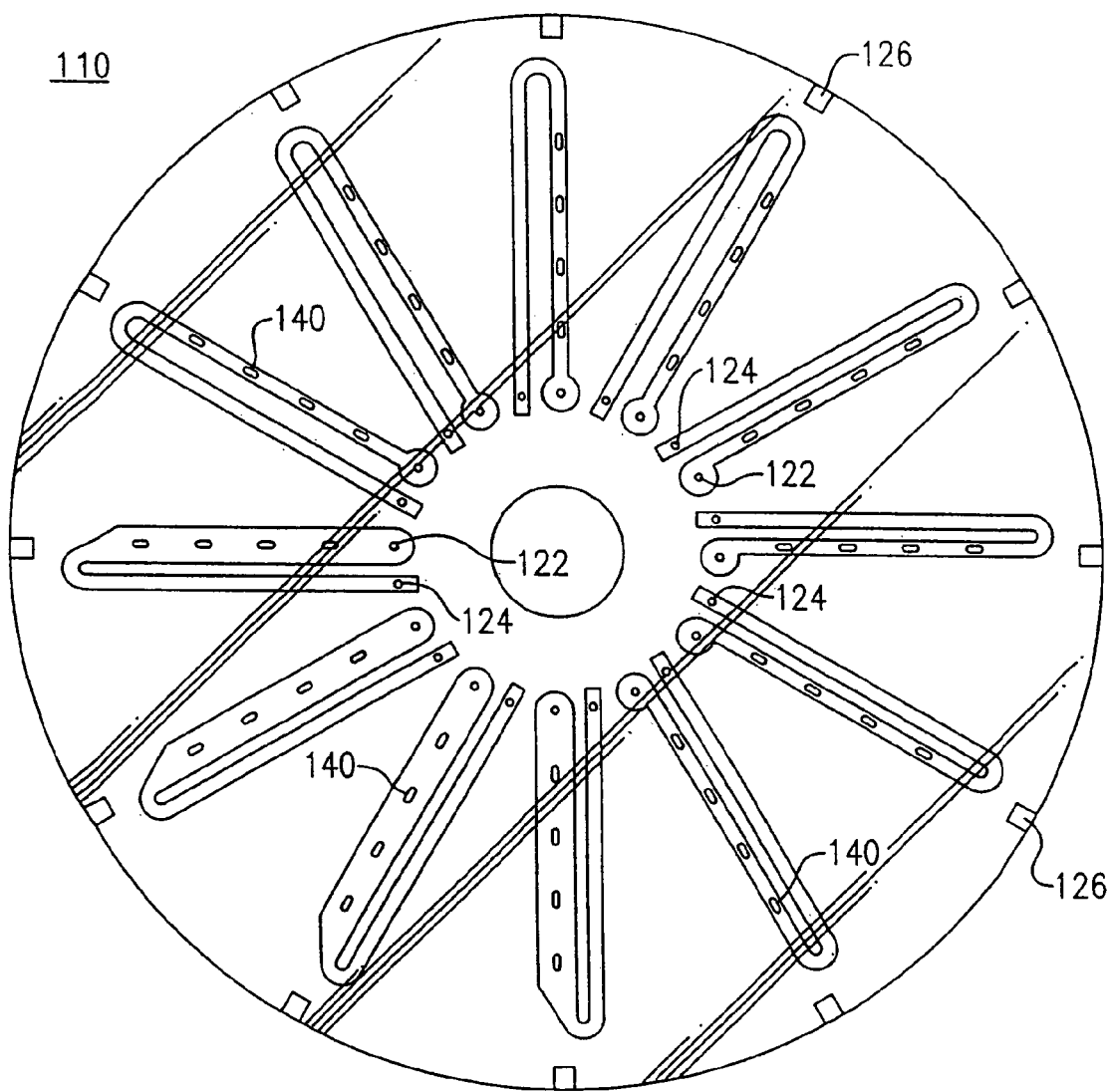
FIG. 3 is a top plan view of the disc shown in FIG. 2.

FIG. 3 is a top plan view of the optical bio-disc 110 illustrated in FIG. 2 with the reflective layer 146 on the cap portion 116 shown as transparent to reveal the fluidic circuits 128, the target zones 140, and trigger markings 126 situated within the disc.

Figure 4:
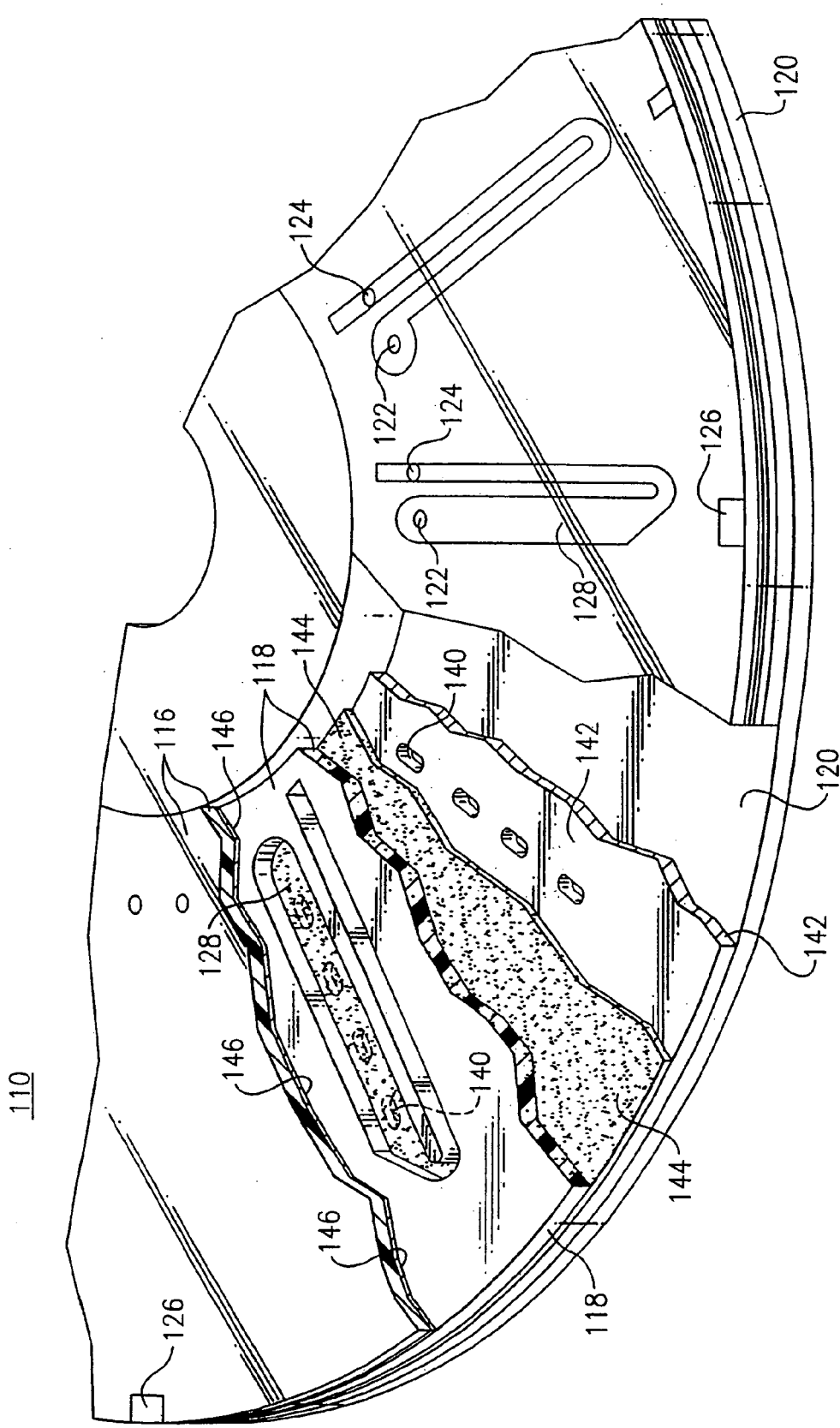
FIG. 4 is a perspective view of the disc illustrated in FIG. 2 with cut-away sections showing the different layers of the disc.

FIG. 4 is an enlarged perspective view of the reflective zone type optical bio-disc 110 according to one embodiment that may be used in the invention. This view includes a portion of the various layers thereof, cut away to illustrate a partial sectional view of each principal layer, substrate, coating, or membrane. FIG. 4 shows the substrate 120 that is coated with the reflective layer 142. An active layer 144 is applied over the reflective layer 142. In the preferred embodiment, the active layer 144 may be formed from polystyrene. Alternatively, polycarbonate, gold, activated glass, modified glass, or modified polystyrene, for example, polystyrene-co-maleic anhydride, may be used. In addition, hydrogels can be used. Alternatively, as illustrated in this embodiment, the plastic adhesive member 118 is applied over the active layer 144. The exposed section of the plastic adhesive member 118 illustrates the cut out or stamped U-shaped form that creates the fluidic circuits 128. The final principal structural layer in this reflective zone embodiment of the bio-disc is the cap portion 116. The cap portion 116 includes the reflective surface 146 on the bottom thereof. The reflective surface 146 may be made from a metal such as aluminum or gold.

Figure 5:
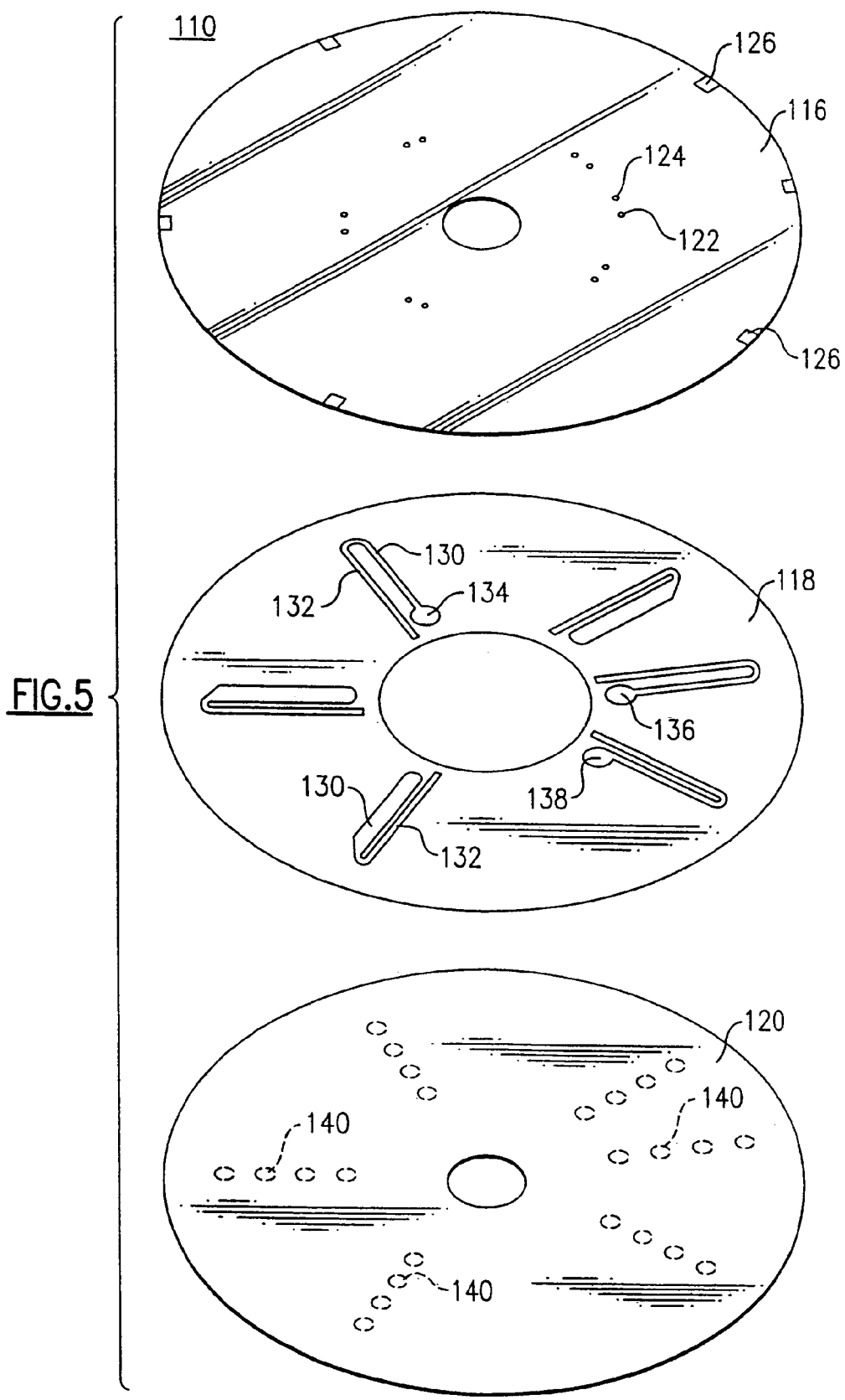
FIG. 5 is an exploded perspective view of a transmissive bio-disc.
Figure 9:
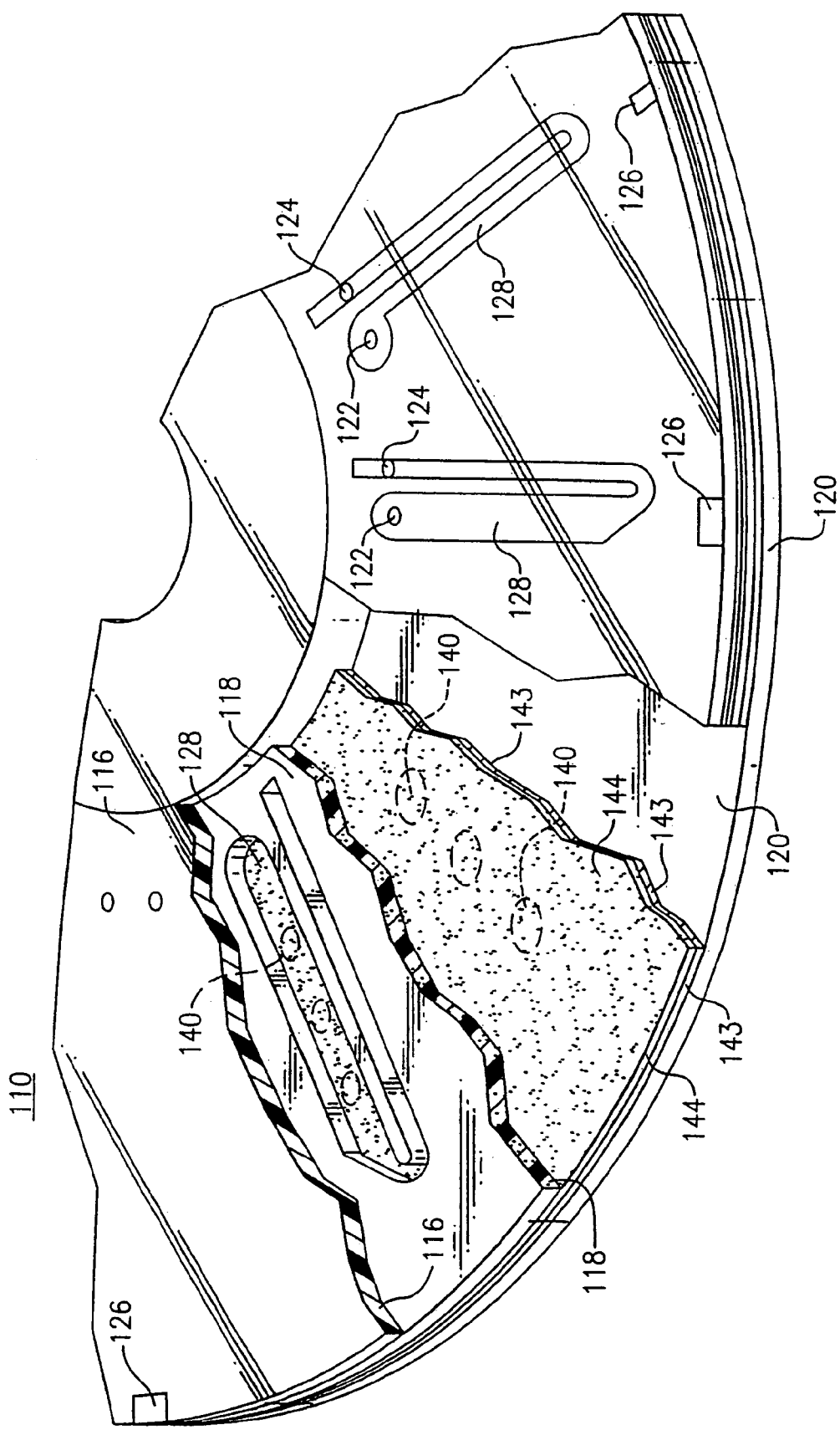
FIG. 9 is a perspective view of the disc illustrated in FIG. 5 with cut-away sections showing the different layers of the disc including the type of semi-reflective layer shown in FIG. 6.

Referring now to FIG. 5, there is shown an exploded perspective view of the principal structural elements of a transmissive type of optical bio-disc 110. The principal structural elements of the transmissive type of optical bio-disc 110 similarly include the cap portion 116, the adhesive or channel member 118, and the substrate 120 layer. The cap portion 116 includes one or more inlet ports 122 and one or more vent ports 124. The cap portion 116 may be formed from a polycarbonate layer. Optional trigger markings 126 may be included on the surface of a thin semi-reflective layer 143, as best illustrated in FIGS. 6 and 9. Trigger markings 126 may include a clear window in all three layers of the bio-disc, an opaque area, or a reflective or semi-reflective area encoded with information that sends data to a processor 166, FIG. 10, which in turn interacts with the operative functions of an interrogation beam 152, FIGS. 6 and 10.

The second element shown in FIG. 5 is the adhesive member or channel layer 118 having fluidic circuits 128 or U-channels formed therein. The fluidic circuits 128 are formed by stamping or cutting the membrane to remove plastic film and form the shapes as indicated. Each of the fluidic circuits 128 includes the flow channel 130 and the return channel 132. Some of the fluidic circuits 128 illustrated in FIG. 5 include a mixing chamber 134. Two different types of mixing chambers 134 are illustrated. The first is a symmetric mixing chamber 136 that is symmetrically formed relative to the flow channel 130. The second is an off-set mixing chamber 138. The off-set mixing chamber 138 is formed to one side of the flow channel 130 as indicated.

Figure 12:
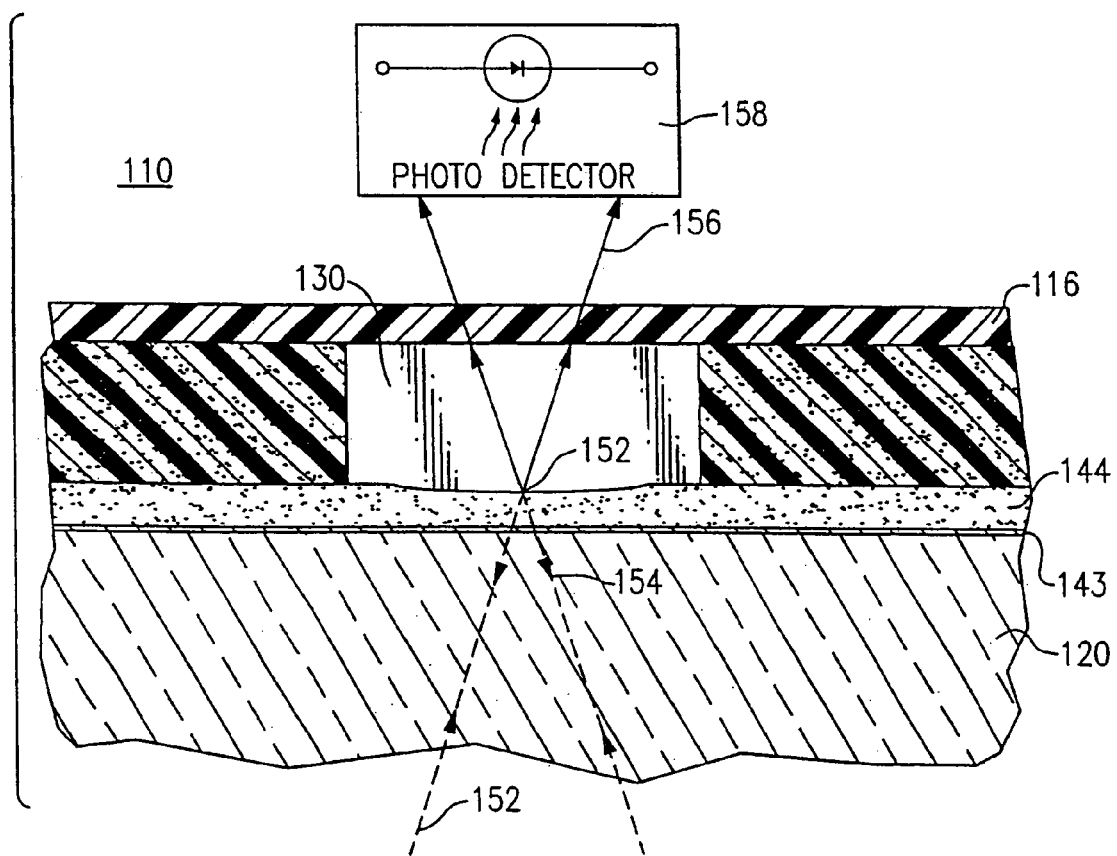
FIG. 12 is a partial cross sectional view taken perpendicular to a radius of the transmissive optical bio-disc illustrated in FIGS. 5, 8, and 9 showing a flow channel formed therein and a top detector.

The third element illustrated in FIG. 5 is the substrate 120 which may include target or capture zones 140. The substrate 120 is preferably made of polycarbonate and has the aforementioned thin semi-reflective layer 143 deposited on the top thereof, FIG. 6. The semi-reflective layer 143 associated with the substrate 120 of the disc 110 illustrated in FIGS. 5 and 6 is significantly thinner than the reflective layer 142 on the substrate 120 of the reflective disc 110 illustrated in FIGS. 2, 3 and 4. The thinner semi-reflective layer 143 allows for some transmission of the interrogation beam 152 through the structural layers of the transmissive disc as shown in FIGS. 6 and 12. The thin semi-reflective layer 143 may be formed from a metal such as aluminum or gold.

FIG. 6 is an enlarged perspective view of the substrate 120 and semi-reflective layer 143 of the transmissive embodiment of the optical bio-disc 110 illustrated in FIG. 5. The thin semi-reflective layer 143 may be made from a metal such as aluminum or gold. In the preferred embodiment, the thin semi-reflective layer 143 of the transmissive disc illustrated in FIGS. 5 and 6 is approximately 100–300 Å thick and does not exceed 400 Å. This thinner semi-reflective layer 143 allows a portion of the incident or interrogation beam 152 to penetrate and pass through the semi-reflective layer 143 to be detected by a top detector 158, FIGS. 10 and 12, while some of the light is reflected or returned back along the incident path. As indicated below, Table 1 presents the reflective and transmissive characteristics of a gold film relative to the thickness of the film layer is fully reflective at a thickness greater than 800 Å. While the threshold density for transmission of light through the gold film is approximately 400 Å.

Figure 7:
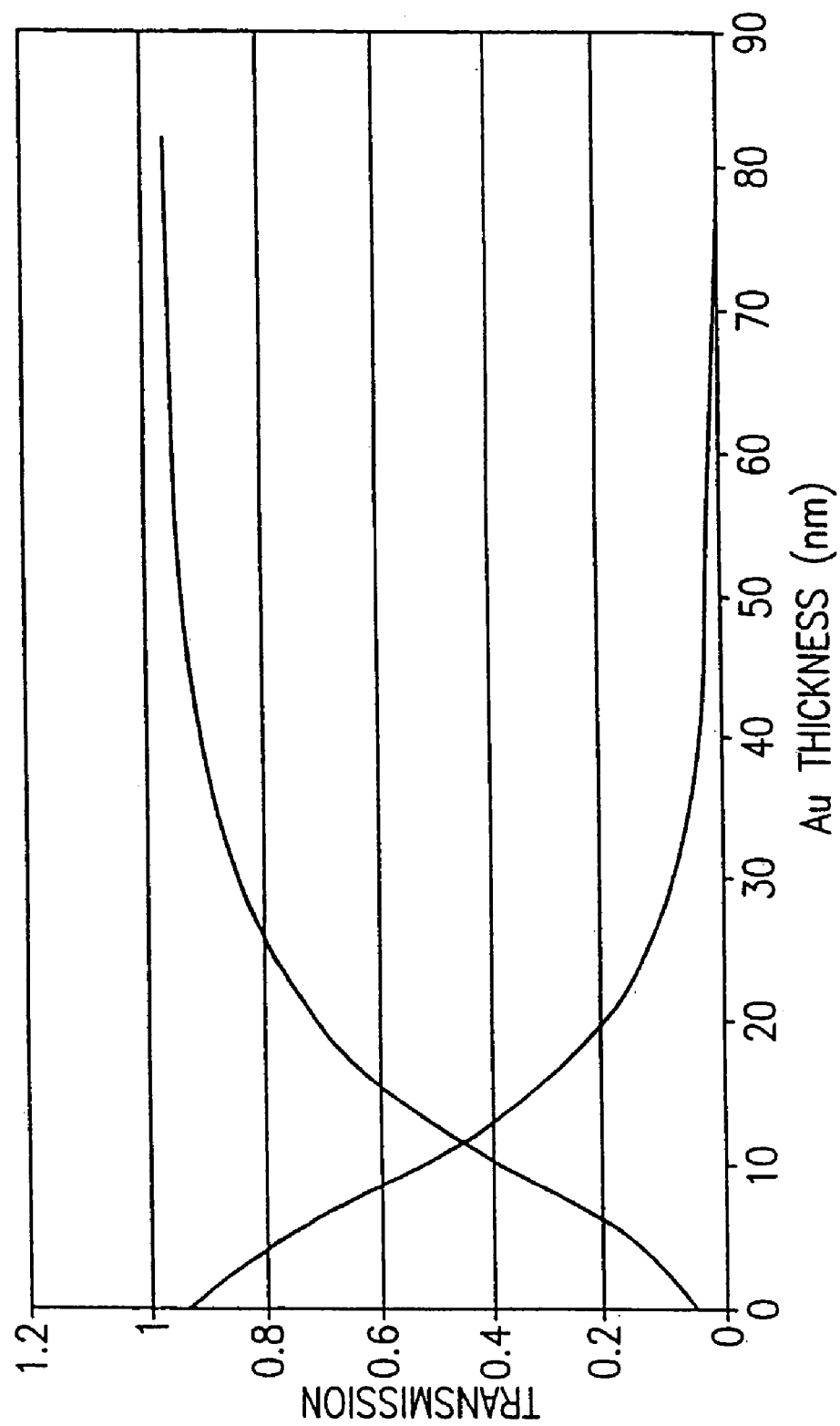
FIG. 7 is a graphical representation showing the relationship between thickness and transmission of a thin gold film.

In addition to Table 1, FIG. 7 provides a graphical representation of ship of the reflective and transmissive nature of the thin semi-reflective layer 143 based upon the thickness of the gold. Reflective and transmissive values used in the graph illustrated in FIG. 7 are absolute values.

TABLE 1

Au film Reflection and Transmission (Absolute Values)

| Thickness (Angstroms) | Thickness (nm) | (i) reflectance | (a) transmittance |
|---|---|---|---|
| 0 | 0 | 0.0505 | 0.9495 |
| 50 | 5 | 0.1683 | 0.7709 |
| 100 | 10 | 0.3981 | 0.5169 |
| 150 | 15 | 0.5873 | 0.3264 |
| 200 | 20 | 0.7142 | 0.2057 |
| 250 | 25 | 0.7959 | 0.1314 |
| 300 | 30 | 0.8488 | 0.0851 |
| 350 | 35 | 0.8836 | 0.0557 |
| 400 | 40 | 0.9067 | 0.0368 |
| 450 | 45 | 0.9222 | 0.0244 |
| 500 | 50 | 0.9328 | 0.0163 |
| 550 | 55 | 0.9399 | 0.0109 |
| 600 | 60 | 0.9448 | 0.0073 |
| 650 | 65 | 0.9482 | 0.0049 |
| 700 | 70 | 0.9505 | 0.0033 |
| 750 | 75 | 0.9520 | 0.0022 |
| 800 | 80 | 0.9531 | 0.0015 |

Figure 8:
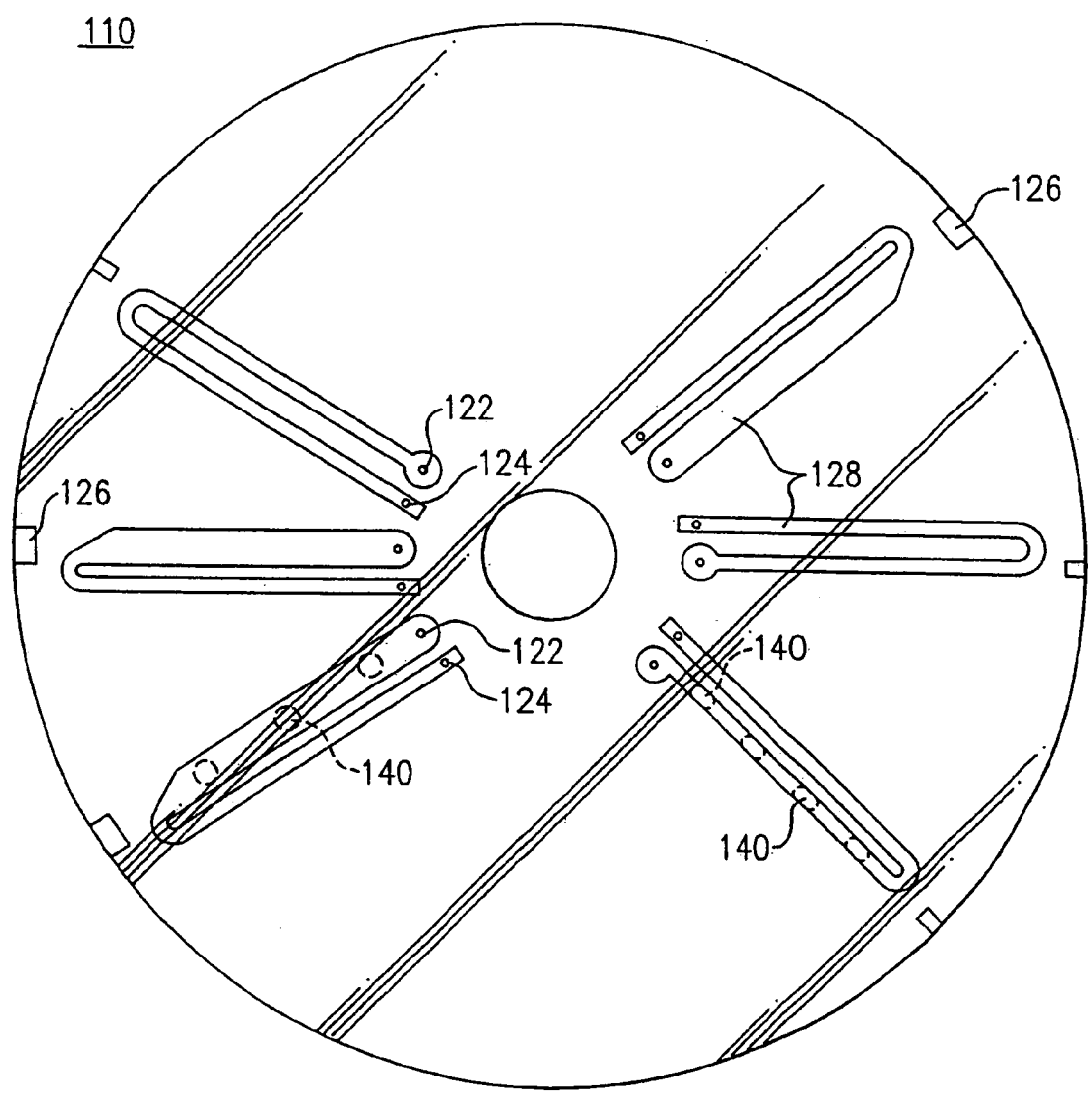
FIG. 8 is a top plan view of the disc shown in FIG. 5.

With reference next to FIG. 8, there is shown a top plan view of the transmissive type optical bio-disc 110 illustrated in FIGS. 5 and 6 with the transparent cap portion 116 revealing the fluidic channels, the trigger markings 126, and the target zones 140 as situated within the disc.

FIG. 9 is an enlarged perspective view of the optical bio-disc 110 according to the transmissive disc embodiment. The disc 110 is illustrated with a portion of the various layers thereof cut away to show a partial sectional view of each principal layer, substrate, coating, or membrane. FIG. 9 illustrates a transmissive disc format with the clear cap portion 116, the thin semi-reflective layer 143 on the substrate 120, and trigger markings 126. In this embodiment, trigger markings 126 include opaque material placed on the top portion of the cap. Alternatively the trigger marking 126 may be formed by clear, non-reflective windows etched on the thin reflective layer 143 of the disc, or any mark that absorbs or does not reflect the signal coming from a trigger detector 160, FIG. 10. FIG. 9 also shows the target zones 140 formed by marking the designated area in the indicated shape or alternatively in any desired shape. Markings to indicate the target zone 140 may be made on the thin semi-reflective layer 143 on the substrate 120 or on the bottom portion of the substrate 120 (under the disc). Alternatively, the target zones 140 may be formed by a masking technique that includes masking the entire thin semi-reflective layer 143 except the target zones 140. In this embodiment, target zones 140 may be created by applying silk screening ink onto the thin semi-reflective layer 143. In the transmissive disc format illustrated in FIGS. 5, 8, and 9, the target zones 140 may alternatively be defined by address information encoded on the disc. In this embodiment, target zones 140 do not include a physically discernable edge boundary.

With continuing reference to FIG. 9, an active layer 144 is illustrated as applied over the thin semi-reflective layer 143. In the preferred embodiment, the active layer 144 is a 10 to 200 μm thick layer of 2% polystyrene. Alternatively, polycarbonate, gold, activated glass, modified glass, or modified polystyrene, for example, polystyrene-co-maleic anhydride, may be used. In addition, hydrogels can be used. As illustrated in this embodiment, the plastic adhesive member 118 is applied over the active layer 144. The exposed section of the plastic adhesive member 118 illustrates the cut out or stamped U-shaped form that creates the fluidic circuits 128.

The final principal structural layer in this transmissive embodiment of the bio-disc 110 is the clear, non-reflective cap portion 116 that includes inlet ports 122 and vent ports 124.

Referring now to FIG. 10, there is a representation in perspective and block diagram illustrating optical components 148, a light source 150 that produces the incident or interrogation beam 152, a return beam 154, and a transmitted beam 156. In the case of the reflective bio-disc illustrated in FIG. 4, the return beam 154 is reflected from the reflective surface 146 of the cap portion 116 of the optical bio-disc 110. In this reflective embodiment of the optical bio-disc 110, the return beam 154 is detected and analyzed for the presence of signal elements by a bottom detector 157. In the transmissive bio-disc format, on the other hand, the transmitted beam 156 is detected, by the aforementioned top detector 158, and is also analyzed for the presence of signal elements. In the transmissive embodiment, a photo detector may be used as top detector 158.

FIG. 10 also shows a hardware trigger mechanism that includes the trigger markings 126 on the disc and the aforementioned trigger detector 160. The hardware triggering mechanism is used in both reflective bio-discs (FIG. 4) and transmissive bio-discs (FIG. 9). The triggering mechanism allows the processor 166 to collect data only when the interrogation beam 152 is on a respective target zone 140, e.g. at a predetermined reaction site. Furthermore, in the transmissive bio-disc system, a software trigger may also be used. The software trigger uses the bottom detector to signal the processor 166 to collect data as soon as the interrogation beam 152 hits the edge of a respective target zone 140. FIG. 10 further illustrates a drive motor 162 and a controller 164 for controlling the rotation of the optical bio-disc 110. FIG. 10 also shows the processor 166 and analyzer 168 implemented in the alternative for processing the return beam 154 and transmitted beam 156 associated with the transmissive optical bio-disc.

Figure 11:
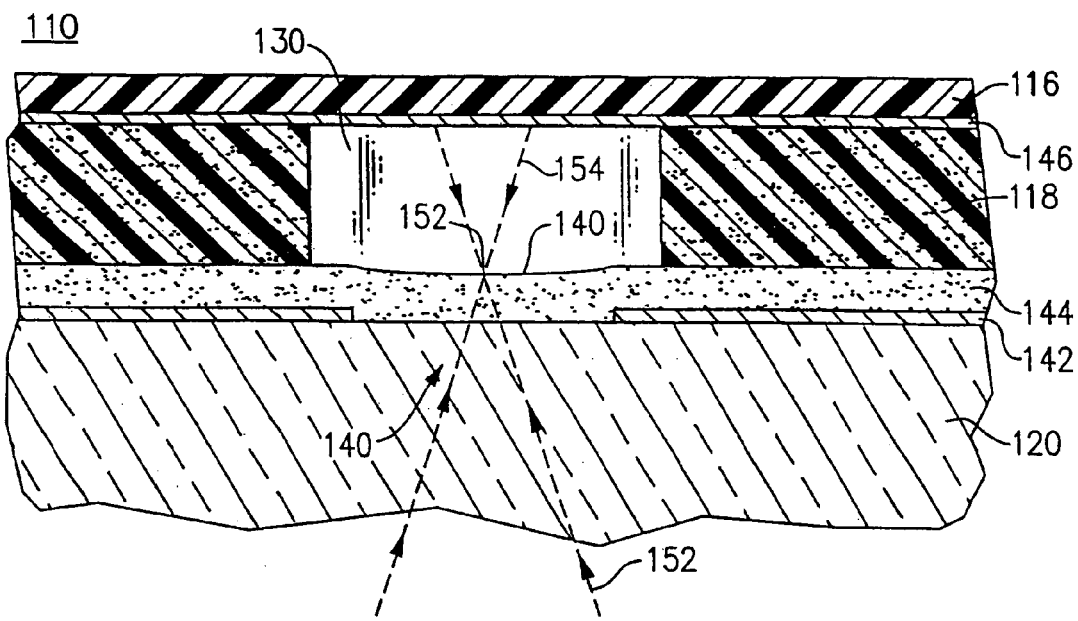
FIG. 11 is a partial cross sectional view taken perpendicular to a radius of the reflective optical bio-disc illustrated in FIGS. 2, 3, and 4 showing a flow channel formed therein.

As shown in FIG. 11, there is presented a partial cross sectional view of the reflective disc embodiment of the optical bio-disc 110. FIG. 11 illustrates the substrate 120 and the reflective layer 142. As indicated above, the reflective layer 142 may be made from a material such as aluminum, gold or other suitable reflective material. In this embodiment, the top surface of the substrate 120 is smooth. FIG. 11 also shows the active layer 144 applied over the reflective layer 142. As also shown in FIG. 11, the target zone 140 is formed by removing an area or portion of the reflective layer 142 at a desired location or, alternatively, by masking the desired area prior to applying the reflective layer 142. As further illustrated in FIG. 11, the plastic adhesive member 118 is applied over the active layer 144. FIG. 11 also shows the cap portion 116 and the reflective surface 146 associated therewith. Thus when the cap portion 116 is applied to the plastic adhesive member 118 including the desired cutout shapes, flow channel 130 is thereby formed. As indicated by the arrowheads shown in FIG. 11, the path of the incident beam 152 is initially directed toward the substrate 120 from below the disc 110. The incident beam then focuses at a point proximate the reflective layer 142. Since this focusing takes place in the target zone 140 where a portion of the reflective layer 142 is absent, the incident continues along a path through the active layer 144 and into the flow channel 130. The incident beam 152 then continues upwardly traversing through the flow channel to eventually fall incident onto the reflective surface 146. At this point, the incident beam 152 is returned or reflected back along the incident path and thereby forms the return beam 154.

FIG. 12 is a partial cross sectional view of the transmissive embodiment of the bio-disc 110. FIG. 12 illustrates a transmissive disc format with the clear cap portion 116 and the thin semi-reflective layer 143 on the substrate 120. FIG. 12 also shows the active layer 144 applied over the thin semi-reflective layer 143. In one embodiment, the transmissive disc has the thin semi-reflective layer 143 made from a metal such as aluminum or gold approximately 100–300 Angstroms thick and does not exceed 400 Angstroms. This thin semi-reflective layer 143 allows a portion of the incident or interrogation beam 152, from the light source 150, FIG. 10, to penetrate and pass upwardly through the disc to be detected by top detector 158, while some of the light is reflected back along the same path as the incident beam but in the opposite direction. In this arrangement, the return or reflected beam 154 is reflected from the semi-reflective layer 143. Thus in this manner, the return beam 154 does not enter into the flow channel 130. The reflected light or return beam 154 may be used for tracking the incident beam 152 on pre-recorded information tracks formed in or on the semi-reflective layer 143 as described in more detail in conjunction with FIGS. 13 and 14. In the disc embodiment illustrated in FIG. 12, a physically defined target zone 140 may or may not be present. Target zone 140 may be created by direct markings made on the thin semi-reflective layer 143 on the substrate 120. These marking may be formed using silk screening or any equivalent method. In the alternative embodiment where no physical indicia are employed to define a target zone (such as, for example, when encoded software addressing is utilized) the flow channel 130 in effect may be employed as a confined target area in which inspection of an investigational feature is conducted. The investigational features which can be inspected according to some embodiments include biological, chemical, or organic specimens, test samples, investigational objects, for example, organic material, and similar test objects or target samples. Such investigational features may be imaged on an output monitor. The investigational features may include biological material, and may also include specific chemical reactions and the products and by-products resulting therefrom, such as, any one of a variety of different calorimetric assays. The investigational features can be used for medical assays, but also for other uses, for example, to detect chemicals.

Figure 13:
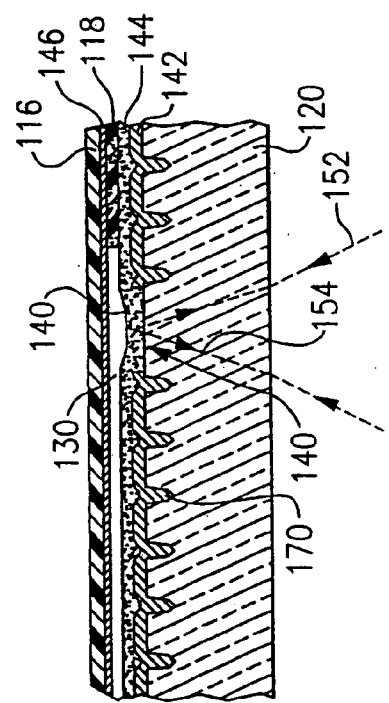
FIG. 13 is a partial longitudinal cross sectional view of the reflective optical bio-disc shown in FIGS. 2, 3, and 4 illustrating a wobble groove formed therein.

FIG. 13 is a cross sectional view taken across the tracks of the reflective disc embodiment of the bio-disc 110. This view is taken longitudinally along a radius and flow channel of the disc. FIG. 13 includes the substrate 120 and the reflective layer 142. In this embodiment, the substrate 120 includes a series of grooves 170. The grooves 170 are in the form of a spiral extending from near the center of the disc toward the outer edge. The grooves 170 are implemented so that the interrogation beam 152 may track along the spiral grooves 170 on the disc. This type of groove 170 is known as a "wobble groove". A bottom portion having undulating or wavy sidewalls forms the groove 170, while a raised or elevated portion separates adjacent grooves 170 in the spiral. The reflective layer 142 applied over the grooves 170 in this embodiment is, as illustrated, conformal in nature. FIG. 13 also shows the active layer 144 applied over the reflective layer 142. As shown in FIG. 13, the target zone 140 is formed by removing an area or portion of the reflective layer 142 at a desired location or, alternatively, by masking the desired area prior to applying the reflective layer 142. As further illustrated in FIG. 13, the plastic adhesive member 118 is applied over the active layer 144. FIG. 13 also shows the cap portion 116 and the reflective surface 146 associated therewith. Thus, when the cap portion 116 is applied to the plastic adhesive member 118 including the desired cutout shapes, the flow channel 130 is thereby formed.

Figure 14:
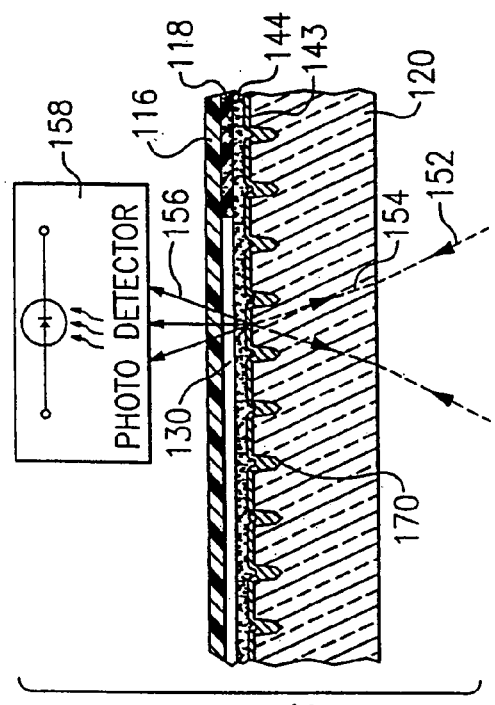
FIG. 14 is a partial longitudinal cross sectional view of the transmissive optical bio-disc illustrated in FIGS. 5, 8, and 9 showing a wobble groove formed therein and a top detector.

FIG. 14 is a cross sectional view taken across the tracks of the transmissive disc embodiment of the bio-disc 110 as described in FIG. 12, for example. This view is taken longitudinally along a radius and flow channel of the disc. FIG. 14 illustrates the substrate 120 and the thin semi-reflective layer 143. This thin semi-reflective layer 143 allows the incident or interrogation beam 152, from the light source 150, to penetrate and pass through the disc to be detected by the top detector 158, while some of the light is reflected back in the form of the return beam 154. The thickness of the thin semi-reflective layer 143 is determined by the minimum amount of reflected light required by the disc reader to maintain its tracking ability. The substrate 120 in this embodiment, like that discussed in FIG. 13, includes the series of grooves 170. The grooves 170 in this embodiment are also preferably in the form of a spiral extending from near the center of the disc toward the outer edge. The grooves 170 are implemented so that the interrogation beam 152 may track along the spiral. FIG. 14 also shows the active layer 144 applied over the thin semi-reflective layer 143. As further illustrated in FIG. 14, the plastic adhesive member or channel layer 118 is applied over the active layer 144. FIG. 14 also shows the cap portion 116 without a reflective surface 146. Thus, when the cap is applied to the plastic adhesive member 118 including the desired cutout shapes, the flow channel 130 is thereby formed and a part of the incident beam 152 is allowed to pass therethrough substantially unreflected.

Figure 15:
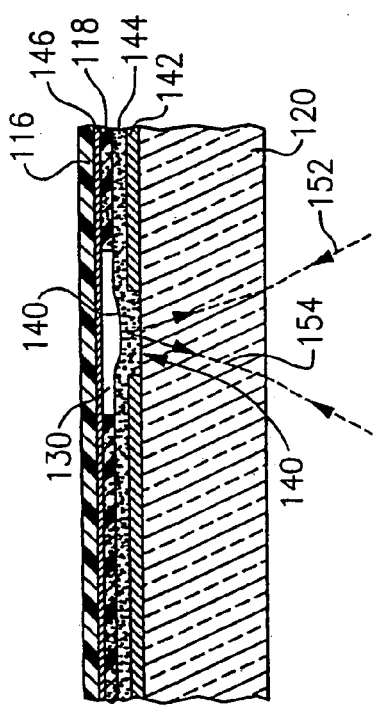
FIG. 15 partial cross sectional view taken perpendicular to a radius of a reflective optical bio-disc showing the entire thickness of the reflective disc and the initial refractive property thereof.
Figure 16:
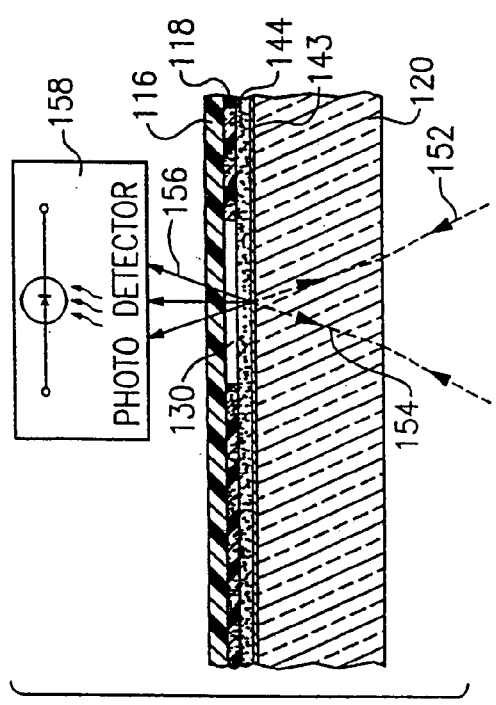
FIG. 16 is a partial cross sectional view taken perpendicular to a radius of a transmissive optical bio-disc showing the entire thickness of the transmissive disc and the initial refractive property thereof.

FIG. 15 is a cross-sectional view similar to FIG. 11 taken perpendicular to a radius of a reflective optical bio-disc and showing the entire thickness of the reflective disc and the initial refractive property thereof. FIG. 16 is a cross-sectional view similar to FIG. 12 taken perpendicular to a radius of a transmissive optical bio-disc and showing the entire thickness of the transmissive disc and the initial refractive property thereof. Grooves 170 are not seen in FIGS. 15 and 16 since the sections are cut along the grooves 170. FIGS. 15 and 16 show the presence of the narrow flow channel 130 that is situated perpendicular to the grooves 170 in these embodiments. FIGS. 13, 14, 15, and 16 show the entire thickness of the respective reflective and transmissive discs. In these figures, the incident beam 152 is illustrated as it appears when initially interacting with the substrate 120 which has refractive properties that change the path of the incident beam as illustrated to provide focusing of the beam 152 on the reflective layer 142 or the thin semi-reflective layer 143.

Counting Methods and Related Software

A number of methods and related algorithms for counting white blood cell using optical disc data are herein discussed in further detail. These methods and related algorithms are not limited to counting white blood cells, but may be readily applied to conducting counts of any type of particulate matter including, but not limited to, red blood cells, white blood cells, beads, and any other objects, both biological and non-biological, that produce similar optical signatures that can be detected by an optical reader.

Figure 17:
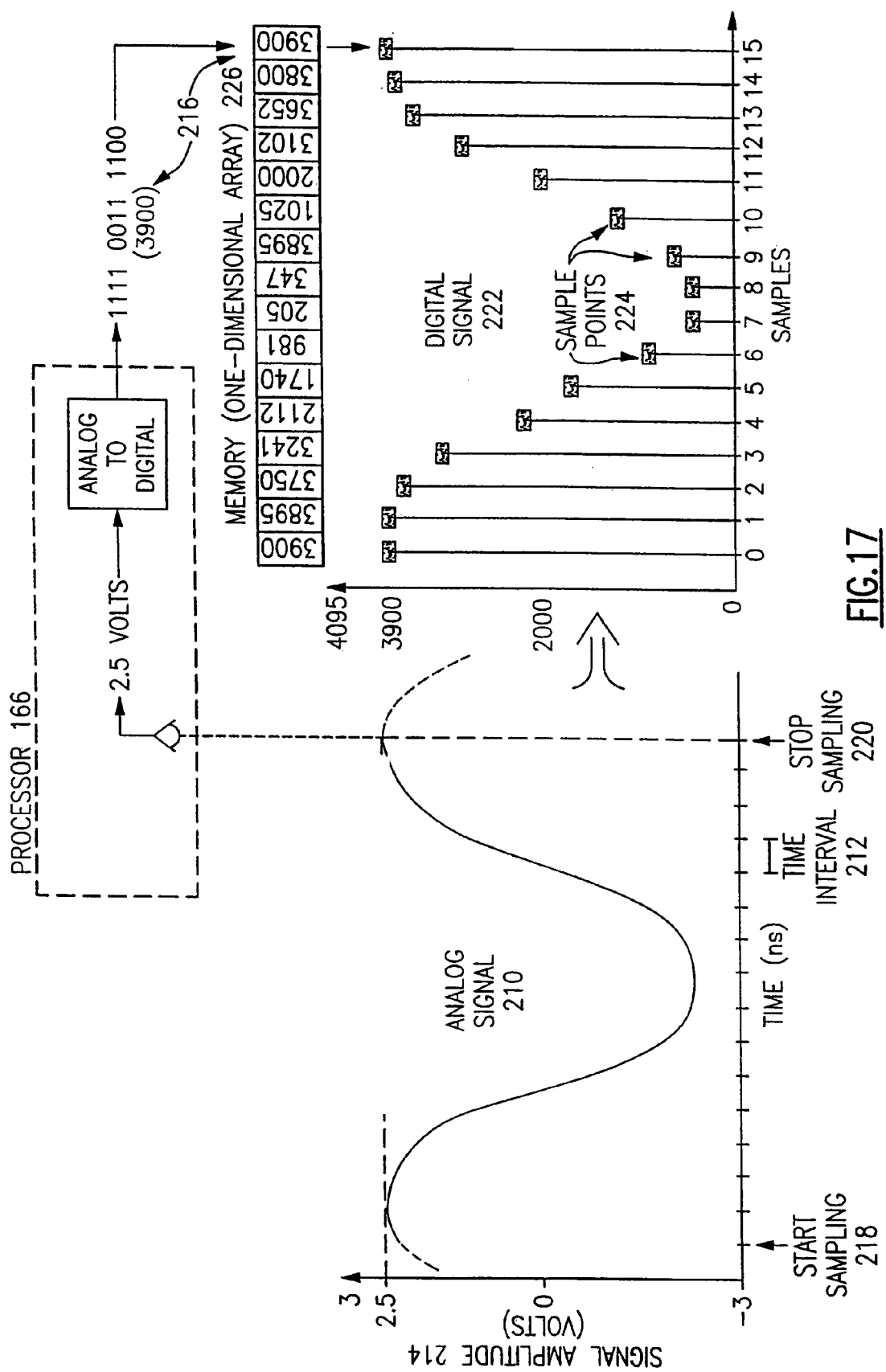
FIG. 17 is a pictorial graphical representation of the transformation of a sampled analog signal to a corresponding digital signal that is stored as a one-dimensional array.

For the purposes of illustration, the following description of the methods and algorithms related to embodiments of the invention as described with reference to FIG. 17 are directed to cell counting. Similar methods and algorithms can be applied to counting other types of objects similar in size to cells. The data evaluation aspects of the cell counting methods and algorithms are described generally herein and can be applied to the methods and apparatus of embodiments of the invention. Methods and algorithms for capturing and processing investigational data from the optical bio-disc have general broad applicability. Such methods and algorithms have been disclosed in further detail in commonly assigned U.S. Provisional Application No. 60/291,233 entitled "Variable Sampling Control For Rendering Pixelation of Analysis Results In Optical Bio-Disc Assembly And Apparatus Relating Thereto" filed May 16, 2001, which is herein incorporated by reference, and the U.S. Provisional Application No. 60/404,921 entitled "Methods For Differential Cell Counts Including Related Apparatus And Software For Performing Same" filed on Aug. 21, 2002, which is herein incorporated by reference.

In the following discussion, the basic scheme of the methods and algorithms is presented with a brief explanation. As illustrated in FIG. 10, information concerning attributes of the biological test sample is retrieved from the optical bio-disc 110 in the form of a beam of electromagnetic radiation that has been modified or modulated by interaction with the test sample. In the case of the reflective optical bio-disc discussed in conjunction with FIGS. 2, 3, 4, 11, 13, and 15, the return beam 154 carries the information about the biological sample. As discussed above, such information about the biological sample is contained in the return beam essentially only when the incident beam is within the flow channel 130 or target zones 140, and is in contact with the sample, according to one embodiment. In the reflective embodiment of the bio-disc 110, the return beam 154 may also carry information encoded in or on the reflective layer 142 or otherwise encoded in the wobble grooves 170 illustrated in FIGS. 13 and 14. As is apparent to one of skill in the art, pre-recorded information is contained in the return beam 154 of the reflective disc with target zones, only when the corresponding incident beam is in contact with the reflective layer 142. Such information is not contained in the return beam 154 when the incident beam 152 is in an area where the information bearing reflective layer 142 has been removed or is otherwise absent. In the case of the transmissive optical bio-disc discussed in conjunction with FIGS. 5, 6, 8, 9, 12, 14, and 16, the transmitted beam 156 carries the information about the biological sample.

With continuing reference to FIG. 10, the information about the biological test sample, whether it is obtained from the return beam 154 of the reflective disc or the transmitted beam 156 of the transmissive disc, is directed to processor 166 for signal processing. This processing involves transformation of the analog signal detected by the bottom detector 157 (reflective disc) or the top detector 158 (transmissive disc) to a discrete digital form.

Referring next to FIG. 17, it is seen that the signal transformation involves sampling the analog signal 210 at fixed time intervals 212, and encoding the corresponding instantaneous analog amplitude 214 of the signal as a discrete binary integer 216. Sampling is started at some start time 218 and stopped at some end time 220. The two common values associated with any analog-to-digital conversion process are sampling frequency and bit depth. The sampling frequency, also called the sampling rate, is the number of samples taken per unit time. A higher sampling frequency yields a smaller time interval 212 between consecutive samples, which results in a higher fidelity of the digital signal 222 compared to the original analog signal 210. Bit depth is the number of bits used in each sample point to encode the sampled amplitude 214 of the analog signal 210. The greater the bit depth, the better the binary integer 216 will approximate the original analog amplitude 214. In one preferred embodiment, the sampling rate is 8 MHz with a bit depth of 12 bits per sample, allowing an integer sample range of 0 to 4095 (0 to $(2n-1)$), where n is the bit depth. This combination may change to accommodate the particular accuracy necessary in other embodiments. By way of example and not limitation, it may be desirable to increase sampling frequency in embodiments involving methods for counting beads, which are generally smaller than cells. The sampled data is then sent to processor 166 for analog-to-digital transformation.

During the analog-to-digital transformation, each consecutive sample point 224 along the laser path is stored consecutively on disc or in memory as a one-dimensional array 226. Each consecutive track contributes an independent one-dimensional array, which yields a two-dimensional array 228 that is analogous to an image.

Blood Separation in Bio-discs using Membranes

The embodiments illustrated in FIGS. 18–22 show various components of a bio-disc with lateral flow circuits for separating human plasma from whole blood. The bio-disc is also herein referred to as bio-compact disc, compact bio-disc, optical bio-disc or optical analysis disc. The lateral flow circuits illustrated in FIGS. 18–20 were designed for use in lateral flow assays on rotating substrates such as the bio-disc 110.

Figure 18:
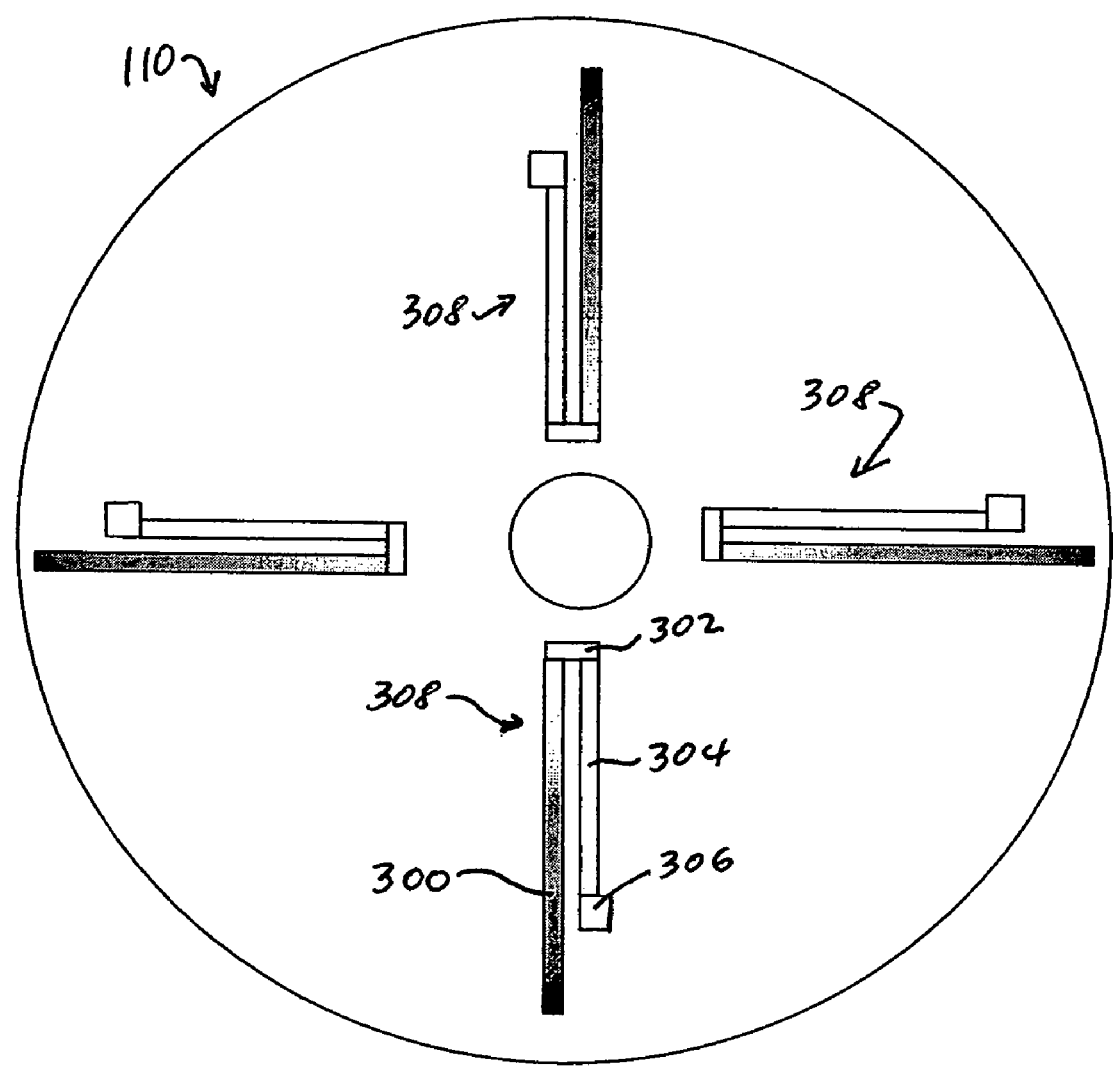
FIG. 18 is a top plan view of the optical bio-disc having four sets of lateral flow circuits.

Referring to FIG. 18, the lateral flow circuit 308 of an embodiment of the invention can include, but is not limited to, a separation membrane 300 for separating an investigational material, which can be referred to in this embodiment as a blood separation membrane or medium ("BSM") 300. The lateral flow circuit 308 can also include a conjugate release pad ("CRP) 302, an analysis membrane 304, and an absorbent pad 306. When arranged in the specific embodiments depicted in FIGS. 18 and 19, plasma can be efficiently separated from red blood cells and transferred to the conjugate release pad. Separation is achieved using a BSM 300 that traps or captures red blood cells while allowing plasma to pass through and migrate toward the center of the disc to the conjugate release pad. From there plasma is then wicked onto the analysis membrane 304 for analysis. The analysis membrane 304 may be formed from nitrocellulose, for example.

Figure 19:
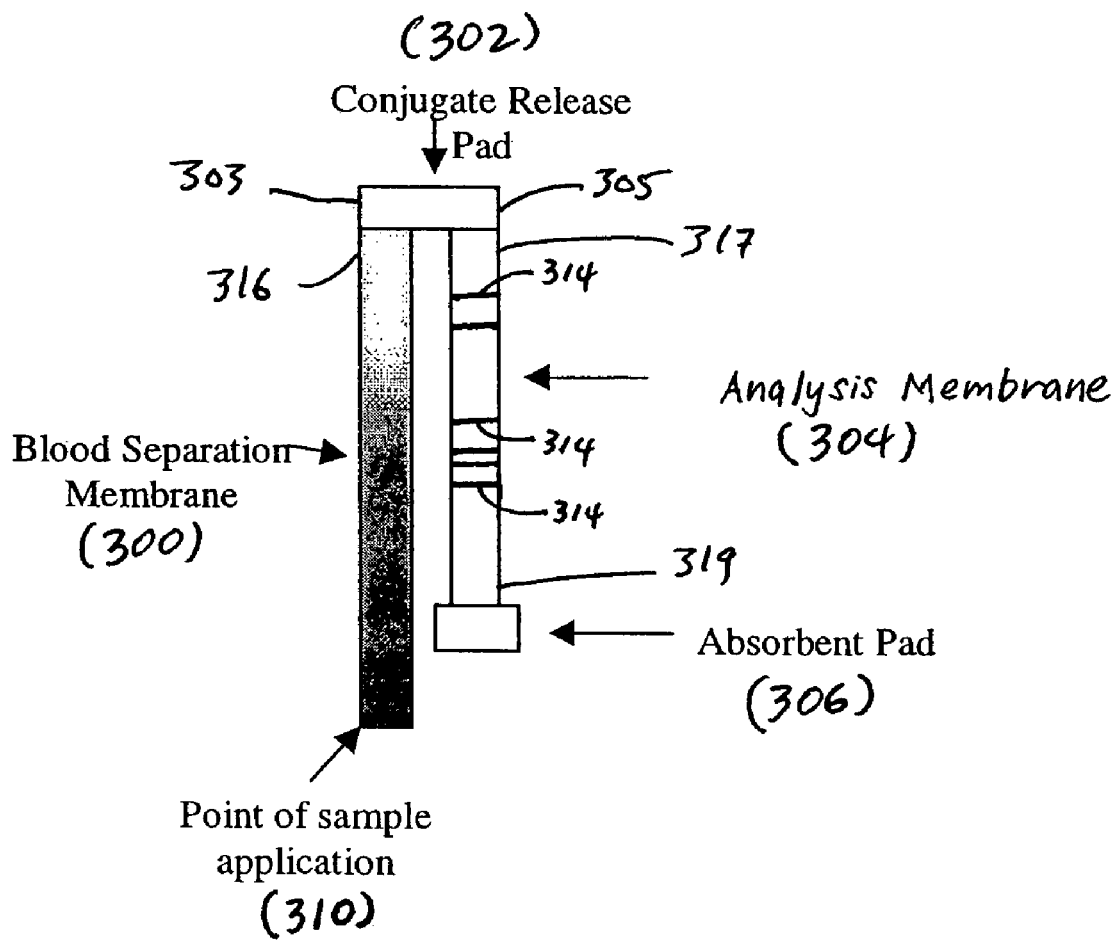
FIG. 19 depicts a detailed view of the lateral flow circuit.

Referring specifically to FIG. 18, there is shown a top plan view of the optical bio-disc 110 having lateral flow circuits 308, according to one embodiment. A close-up view of a lateral flow circuit 308 is shown in FIG. 19. Referring to FIGS. 18 and 19, the lateral flow circuit 308 can include a blood separation membrane or medium 300 having a first end or sample receiving end 310 and a second end 316. The second end 316 of BSM 300 can be connected to a first end 303 of a conjugate release pad ("CRP") 302. The second end 305 of CRP 302 can be connected to a first end 317 of an analysis membrane 304. The second end 319 of analysis membrane 304 can be connected to an absorbent pad 306. The analysis membrane 304 may include one or more capture zones 314. Sample may be applied to the sample receiving end 310 of the BSM 300. The BSM 300 may be formed from, but not limited to, natural and synthetic fiber composites such as BTS-SP asymmetric membranes having graduated pore structures (Pall Corporation), CytoSep Media (Ahlstrom Filtration/Pall Corporation), Presense membrane (Pall Corporation), BTS-SP (Pall Corporation), Hemasep Medium (Pall Corporation), nylon, hydrophilic polyethersulfone, polyethersulfone, acrylic copolymer, polysultone, nitrocellulose, cellulose and any bio-compatible membrane material. According to one embodiment, the BSM 300 membrane is the BTS-SP membrane. The CRP 302, analysis membrane 304, and absorbent pads 306 may also be formed from natural and synthetic fiber composites.

One embodiment of the lateral flow circuit, shown in FIG. 18, may be advantageous when used on the Bio-CD. Due to the nature of the bio-disc system, the disc 110 will spin (centrifuge) while within the drive. In some embodiments, it may be advantageous or even imperative, for certain assays, that no red blood cells ("RBCs") make contact with the analysis membrane 304. A traditional in-line lateral flow assay can be subjected to RBC migration into the analysis membrane due to the centrifugal force. In some embodiments, it is not desirable to have RBCs in the analysis membrane since they may interfere with the assay. The parallel arrangement configuration of the lateral flow circuit of the embodiment shown in FIGS. 18 and 19 can prevent RBC migration onto the analysis membrane 304 thus preventing RBC interference with the assay.

In FIGS. 18 and 19, the lateral flow circuit is shown with the separation membrane 300 and analysis membrane 304 configured substantially parallel and extending in a radial direction of the bio-disc. The CRP 302 connects the separation membrane 300 and analysis membrane 304 at a portion of each membrane that is near the inner perimeter of the bio-disc so that the CRP 302, the separation membrane 300 and the analysis membrane 300 are in fluid communication with each other. Other embodiments are also possible including configurations where the separation membrane 300 and analysis membrane 304 are not parallel, or where each membrane extends in a separate radial direction of the bio-disc such that the membranes substantially form an angle.

Figure 20A:
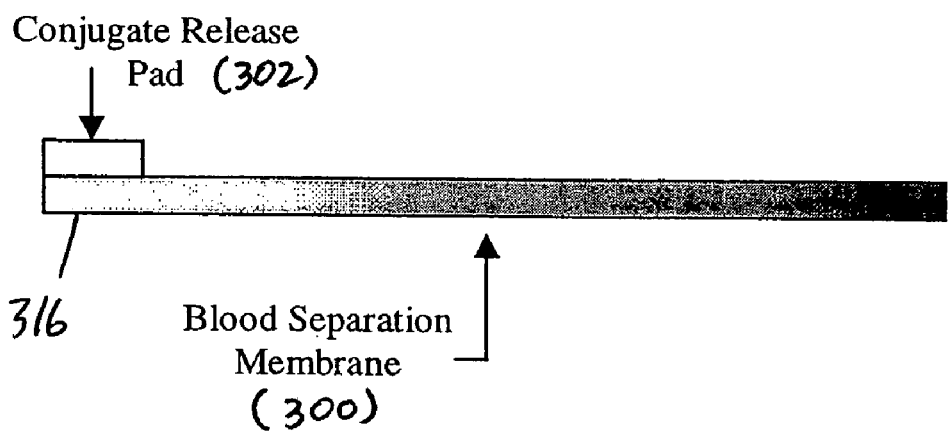
FIG. 20A is a side view of some components of a lateral flow circuit.
Figure 20:
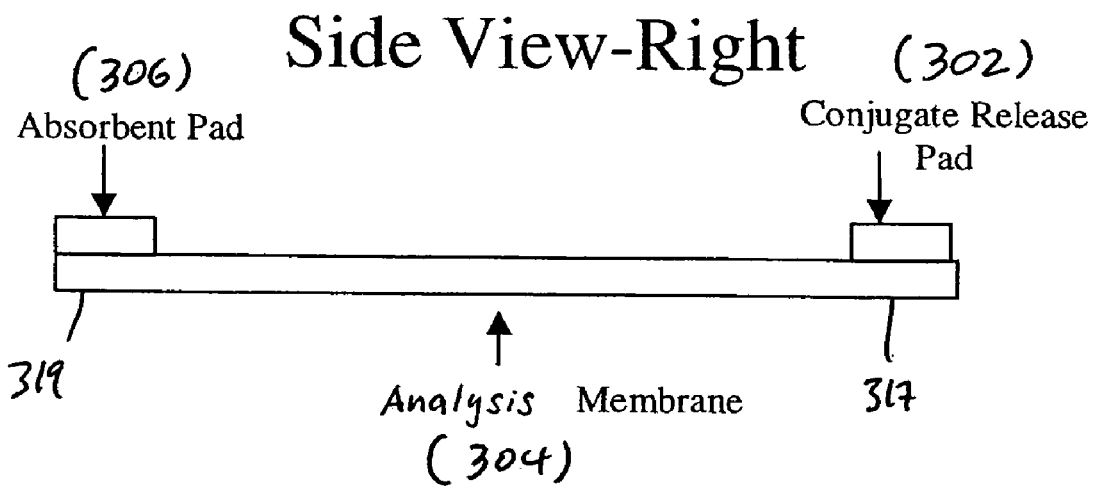
FIG. 20B is a side view of some components of a lateral flow circuit.

Referring next to FIGS. 20A and 20B, there are illustrated side views of the components of the lateral flow circuit 308, according to one embodiment. As shown in FIG. 20A, the BSM 300 is shown with the CRP 302 connected to or in fluid communication with on top of the second end 316 of the BSM 300. As illustrated in FIG. 20B, the CRP 302 may also be connected to or in fluid communication with the top of the first end 317 of the analysis membrane 304 while the absorbent pad 306 can be connected to or in fluid communication with the top of the second end 319 of the analysis membrane 304 to complete the lateral flow circuit 308. Other configurations of the BSM 300, the CRP 302, the analysis membrane 304, and the absorbent pad 306 are possible, where the points of connection or fluid communication are different than illustrated in FIGS. 18–20. For example, in some embodiments the BSM 300 and the analysis membrane 304 are configured so as to from an angle and where the CRP 302 is still connected to or in fluid communication with the BSM 300 and the analysis membrane 304, near, for example, the inner perimeter of the bio-disc. These configurations can be advantageous for an analysis where it is preferred that some matter, for example RBCs, do not migrate to the analysis membrane 304.

Figure 21:
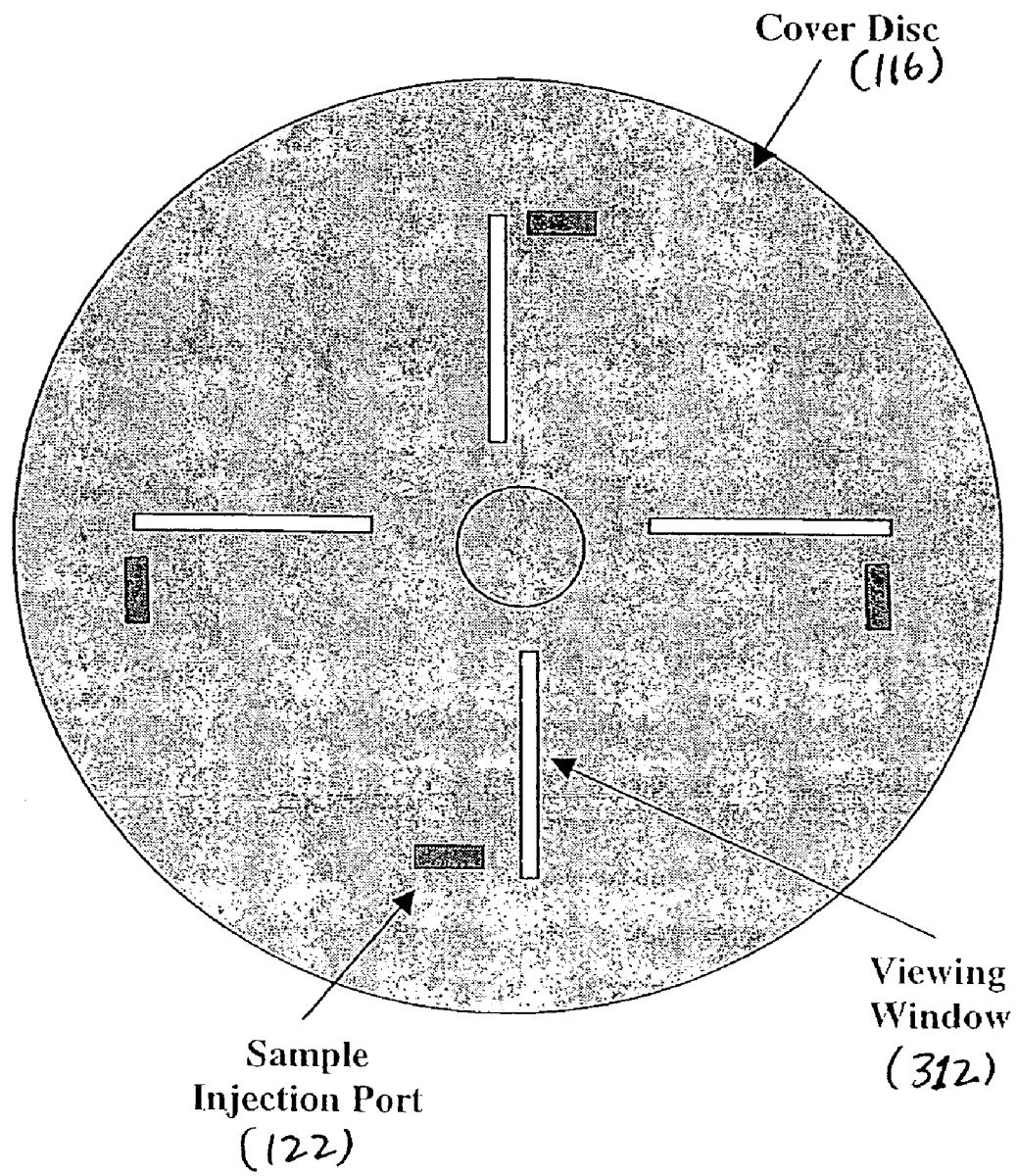
FIG. 21 is a top plan view of a reflective disc for blood separation and analysis having a cover disc.
Figure 22:
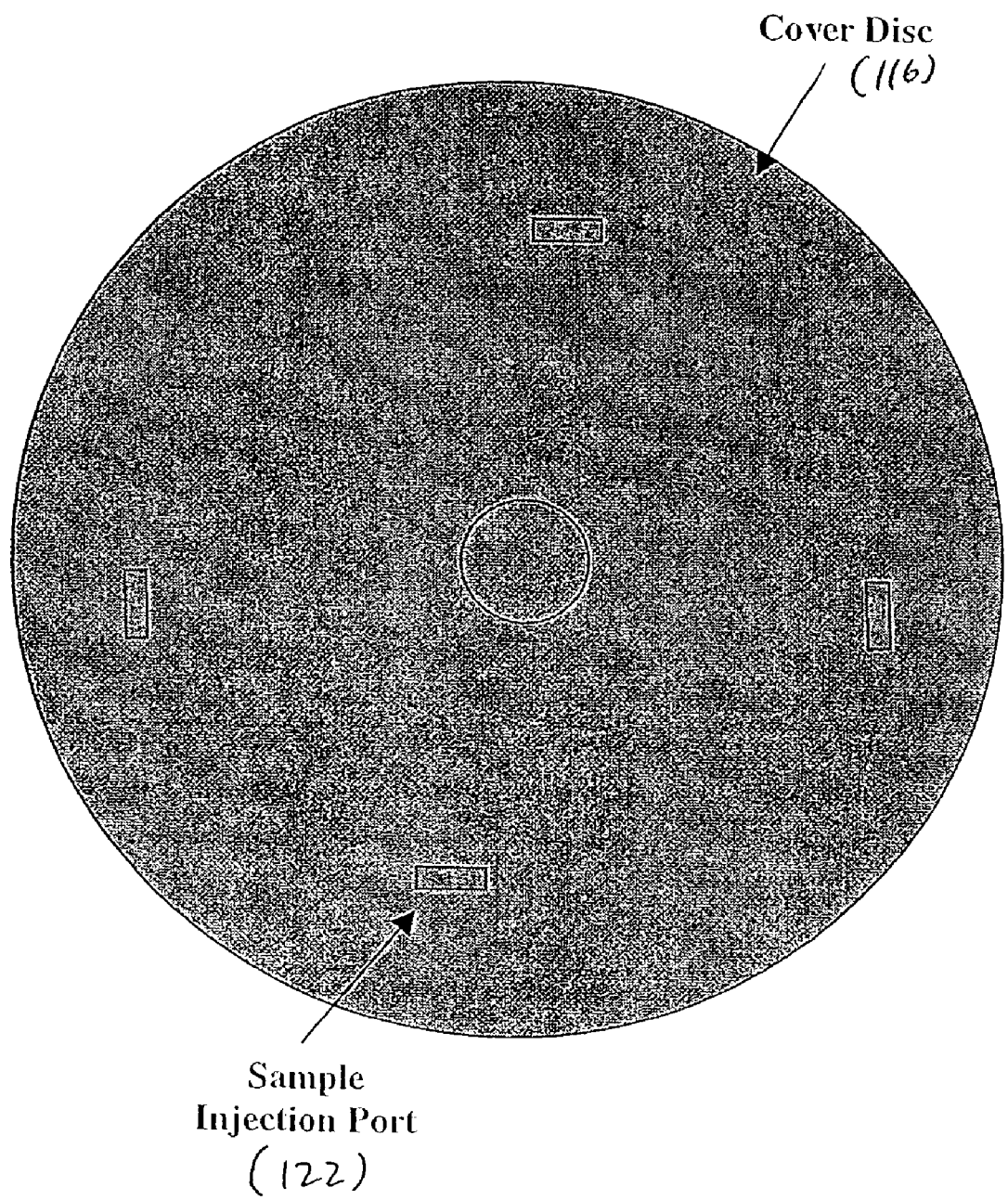
FIG. 22 is a top plan view of a transmissive disc for blood separation and analysis having a cover disc.

The bio-disc may optionally include a cover disc, according to some embodiments. Embodiments of optical bio-discs 110 having cover discs are depicted in FIGS. 21 and 22 wherein a top plan view of a reflective disc for blood separation is shown, in FIG. 21, having a cover disc 116, according to one embodiment. The cover disc 116 can include an inlet port or sample injection port 122. Also shown in FIG. 21 are viewing or analysis windows 312 below which the analysis membrane 304 may be placed for interrogation by a read beam from the optical disc reader 112 (FIG. 1).

Turning next to FIG. 22 there is illustrated a top plan view of one embodiment of a transmissive disc for use in blood separation and serum analysis assays having a cover disc 116 with an inlet port 122 formed therein. In use, a whole blood sample may be loaded into the inlet port 122, of either the reflective or transmissive disc. Serum can then be separated from whole blood by the BSM 300. Following this, serum continues to move through the BSM 300 and into the CRP 302. Reagents may be preloaded on the CRP 302 during assembly of the bio-disc 110. Reagents may include signal elements necessary for detection of analytes in the serum. Signal elements may include, for example, nanoparticles having signal agents attached thereto. Signal agents may include binding proteins, oligonucleotides, antigens, antibodies, DNA, RNA, and the like. The reagents in the CRP may dissolve in the serum and react or bind with analytes in the serum. The resulting mixture, which may be referred to, for example, as a reagent-investigative feature mixture or a reagent-sample mixture, can flow into the analysis membrane.

In some embodiments, the analysis membrane may contain analysis or capture zones 314, as shown in FIG. 19, having capture agents bound thereto. Capture agents may include binding proteins, antigens, antibodies, DNA, RNA, and the like. As the reagent-sample mixture flows through the analysis membrane 304 and into the absorbent pad 306, analytes with the signal elements bound thereto may be captured by the capture elements or agents in the analysis zones. The analysis zones 314 may then be then interrogated using the read beam 152 from the optical disc reader and the reflected signal 154 (FIGS. 10, 11, 13 and 15) or transmitted signal 156 (FIGS. 10, 12, 14 and 16), depending on the type of disc 110 used, may be analyzed to determine the presence and amount of signal agents in the analysis zones 314. Further details relating to detection and quantification of analytes using optical bio-discs and related methods for attaching signal and capture agents onto solid surfaces are disclosed in commonly assigned and co-pending U.S. patent application, Ser. No. 10/348,049 entitled "Multi-Purpose Optical Analysis Disc for Conducting Assays and Related Methods for Attaching Capture Agents" filed Jan. 21, 2003 which is incorporated by reference in its entirety.

All patents, provisional applications, patent applications, and other publications mentioned in this specification are incorporated herein in their entireties by reference.

While this invention has been described in detail with reference to a certain preferred embodiments, it should be appreciated that the invention is not limited to those precise embodiments. Rather, in view of the present disclosure that describes the current best mode for practicing the invention, many modifications and variations would present themselves to those of skill in the art without departing from the scope and spirit of this invention Furthermore, in view of the present disclosure, those skilled in the art will recognize, or be able to ascertain, using no more than routine experimentation, many equivalents to the specific embodiments of the invention described herein.

What is claimed is:

1. An optical bio-disc for blood separation and immuno-hematological analysis, comprising:
    a substrate having an inner perimeter and an outer perimeter;
    a lateral flow circuit positioned between the inner perimeter and the outer perimeter of said substrate, said lateral flow circuit comprising
    a blood separation membrane with a sample receiving portion, said separation membrane having a first end located closer to the inner perimeter than a second end;
    a conjugate release pad attached to the first end of said blood separation membrane;
    an analysis membrane attached at a first end thereof to said conjugate release pad, wherein the first end of the analysis membrane is closer to the inner perimeter than a second end thereof; and
    an absorbent pad in fluid communication with said analysis membrane.

2. The optical bio-disc of claim 1, wherein said analysis membrane comprises nitrocellulose.

3. The optical bio-disc of claim 1, wherein said blood separation membrane comprises at least one of natural fiber and synthetic fiber composites.

4. An optical bio-disc, comprising:
    a substrate having an inner perimeter and an outer perimeter;
    a lateral flow circuit positioned between the inner perimeter and outer perimeter of said substrate, said lateral flow circuit comprising
    a separation membrane for separating an investigational material, the separation membrane having a first portion located closer to the inner perimeter than a second portion thereof;
    an analysis membrane having a first portion located closer to the inner perimeter than a second portion thereof; and
    a conjugate release pad connected to the first portion of the separation membrane and the first portion of the analysis membrane in a configuration defining a connection between said separation membrane and analysis membrane.

5. The bio-disc of claim 4, wherein said lateral flow circuit comprises a blood separation membrane with a sample receiving portion.

6. The bio-disc of claim 4, wherein the lateral flow circuit is configured such that said separation membrane and said analysis membrane are substantially parallel to each other and extend in a radial direction of the bio-disc.

7. The bio-disc of claim 4, wherein the conjugate release pad connects to the separation membrane and the analysis membrane at ends of the first portions of the separation membrane and the analysis membrane that are nearer the inner perimeter of the bio-disc than the rest of said first portions.

8. The bio-disc of claim 4, wherein said conjugate release pad comprises reagents that include signal elements for the detection of analytes.

9. The bio-disc of claim 4, wherein the lateral flow circuit further comprises an absorbent material connected to said analysis membrane.

10. The bio-disc of claim 4, wherein said analysis membrane comprises a capture zone.

11. The bio-disc of claim 10, wherein said capture zone comprises a capture agent for capturing analytes with the signal elements bound thereto.

12. The bio-disc of claim 11, further comprising a cover disc comprising a sample injection port.

13. The bio-disc of claim 12, wherein said cover disc further comprises a viewing window.

14. The bio-disc of claim 12, wherein said substrate and said cover disc is transmissive.

15. An optical bio-disc, comprising:
    a substrate having an inner perimeter and an outer perimeter;
    a lateral flow circuit positioned between the inner perimeter and the outer perimeter of the third substrate, said lateral flow circuit comprising
    a separation membrane for separating an investigational material;
    an analysis membrane; and
    a conjugate release pad in fluid communication with the separation membrane and analysis membrane;
    wherein the lateral flow circuit is configured such that the separation membrane and the analysis membrane are substantially parallel to one another and extend in a radial direction of the bio-disc; and
    wherein the conjugate release pad connects to the separation membrane and the analysis membrane at portions of the separation membrane and the analysis membrane that are nearer the inner perimeter of the bio-disc than other portions thereof.

* * * * *